United States Patent
Varela et al.

(10) Patent No.: US 11,951,170 B2
(45) Date of Patent: Apr. 9, 2024

(54) CHEMICALLY COUPLED TRANSPORTER FOR LOW-HYDROPHOBICITY BIOACTIVE DRUGS INTO THE CENTRAL NERVOUS SYSTEM

(71) Applicants: Skybio LLC, Miami, FL (US); Consejo Nacional de Investigaciones Científicas y Técnicas (Conicet), Ciudad Autónoma de Buenos Aires (AR); Universidad Nacional de Tucumán, Tucumán (AR); Universidad de Buenos Aires, Buenos Aires (AR); Sistema Provincial De Salud De Tucumán, Tucuman (AR)

(72) Inventors: Oscar José Varela, Ciudad Autonoma de Buenos Aires (AR); Rosana Nieves Chehín, Tucumán (AR); Cesar Luis Ávila, Tucumán (AR); Sergio Benjamin Socías, Tucumán (AR); Diego Ploper, Tucumán (AR); Esteban Vera Pingitore, Tucumán (AR); Analía Silvina Chaves, Tucumán (AR); Martin Luong, Ciudad Autónoma de Buenos Aires (AR); Verónica Elena Manzano, Ciudad Autónoma de Buenos Aires (AR); Rodrigo Hernán Tomas Grau, Ciudad Autónoma de Buenos Aires (AR); Maria Florencia González Lizárraga, Tucumán (AR); Adriana Andrea Kolender, Ciudad Autónoma de Buenos Aires (AR); Agustín Osvaldo Pernicone, Ciudad Autónoma de Buenos Aires (AR)

(73) Assignees: Skybio LLC, Miami, FL (US); Consejo Nacional de Investigaciones Científicas y Ténicas (Conicet), Ciudad Autónoma de Buenos Aires (AR); Universidad Nacional de Tucumán, Tucumán (AR); Universidad de Buenos Aires, Buenos Aires (AR); Sistema Provincial De Salud De Tucumán, Tucuman (AR)

( * ) Notice: Subject to any disclaimer, the term of this patent is extended or adjusted under 35 U.S.C. 154(b) by 0 days.

(21) Appl. No.: 18/121,318

(22) Filed: Mar. 14, 2023

(65) Prior Publication Data
US 2023/0218768 A1 Jul. 13, 2023

Related U.S. Application Data

(63) Continuation of application No. PCT/IB2022/050920, filed on Feb. 2, 2022.

(60) Provisional application No. 63/145,190, filed on Feb. 3, 2021.

(51) Int. Cl.
A61K 47/55 (2017.01)

(52) U.S. Cl.
CPC .................... A61K 47/552 (2017.08)

(58) Field of Classification Search
CPC .................................... A61K 47/552
See application file for complete search history.

(56) References Cited

FOREIGN PATENT DOCUMENTS

| WO | 1989/007938 A1 | 9/1989 |
| WO | 2003/030819 A2 | 4/2003 |
| WO | 2003/057169 A2 | 7/2003 |
| WO | 2003/094842 A2 | 11/2003 |
| WO | 2004/064728 A2 | 8/2004 |
| WO | 2020/084168 A1 | 4/2020 |

OTHER PUBLICATIONS

"Global, Regional, and National Burden of Parkinson's Disease, 1990-2016: a Systematic Analysis for the Global Burden of Disease Study 2016", The Lancet, Neurology, vol. 17, No. 11, Nov. 2018, pp. 939-953.
PCT International Search Report and Written Opinion, PCT Patent Application No. PCT/IB2022/050920, dated May 25, 2022, 13 pages.
Alim et al., "Demonstration of a Role for Alpha-Synuclein as a Functional Microtubule-Associated Protein", Journal of Alzheimer's Disease: JAD, vol. 6, No. 4, Aug. 2004, pp. 435-442.

(Continued)

*Primary Examiner* — Brian E McDowell
(74) *Attorney, Agent, or Firm* — Kilpatrick Townsend & Stockton LLP

(57) ABSTRACT

The present disclosure provides a compound comprising a modified tetracycline derivative, covalently coupled through a linker to a low-hydrophobicity bioactive molecule useful for treating neurodegenerative diseases, wherein the modified tetracycline derivative is optionally defined by the following formula:

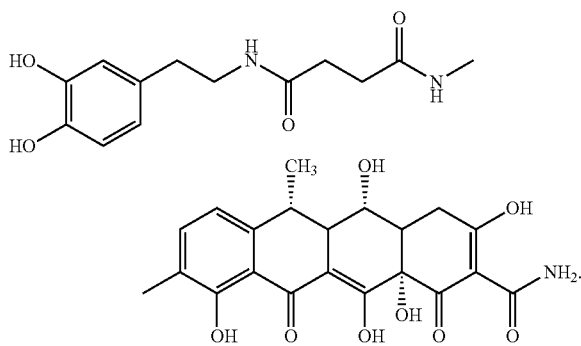

2 Claims, 10 Drawing Sheets

(56) References Cited

OTHER PUBLICATIONS

Araki et al., "Parkinson's Disease is a Type of Amyloidosis Featuring Accumulation of Amyloid Fibrils of α-synuclein", Proceedings of the National Academy of Sciences of the United States of America, vol. 116, No. 36, Sep. 3, 2019, pp. 17963-17969.

Avila et al., "Structural Characterization of Heparin-Induced Glyceraldehyde-3-Phosphate Dehydrogenase Protofibrils Preventing α-Synuclein Oligomeric Species Toxicity", Journal of Biological Chemistry, vol. 289, No. 20, May 16, 2014, pp. 13838-13850.

Barden et al., ""Glycylcyclines". 3. 9-Aminodoxycyclinecarboxamides", Journal of Medicinal Chemistry, vol. 37, No. 20., Sep. 30, 1994, pp. 3205-3211.

Berens et al., "Supporting Information for Subtype Selective Tetracycline Agonists and Their Application for a Two-Stage Regulatory System", ChemBioChem, vol. 7, No. 2, Available Online at: https://doi.org/10.1002/cbic.20060022., Sep. 4, 2006, 26 pages.

Bieschke et al., "Oxidative Metabolites Accelerate Alzheimer's Amyloidogenesis by a Two-step Mechanism, Eliminating the Requirement for Nucleation", Biochemistry, vol. 44, No. 13, Available Online at: 10.1021/bi0501030., Apr. 5, 2005, pp. 4977-4983.

Bortolanza et al., "Tetracycline Repurposing in Neurodegeneration: Focus on Parkinson's Disease" Journal of Neural Transmission, vol. 125, No. 10, Springer Vienna, Vienna, Aug. 14, 2018, pp. 1403-1415.

Bousset et al., "Structural and Functional Characterization of Two Alpha-synuclein Strains", Nature Communications, vol. 4, 2013, 13 pages.

Danzer et al., "Different Species of α-Synuclein Oligomers Induce Calcium Influx and Seeding", The Journal of Neuroscience, vol. 27, No. 34, Aug. 22, 2007, pp. 9220-9232.

Dos-Santos-Pereira et al., "Microglial Glutamate Release Evoked by A-synuclein Aggregates is Prevented by Dopamine", GLIA, vol. 66, No. 11, Nov. 5, 2018, pp. 1-41.

Duda et al., "Neuropathology of Synuclein Aggregates: New Insights into Mechanisms of Neurodegenerative Diseases", Journal of Neuroscience Research, vol. 61, No. 2, Jul. 15, 2000, pp. 121-127.

Eskelinen, "Disturbed Cholesterol Traffic But Normal Proteolytic Function in LAMP-1/LAMP-2 Double-Deficient Fibroblasts", Jul. 2004, 14 pages.

Esposito et al., "Nanoparticulate Lipid Dispersions for Bromocriptine Delivery: Characterization and in Vivo Study", European Journal of Pharmaceutics and Biopharmaceutics, vol. 80, No. 2, Feb. 2012, pp. 306-314.

Esteves et al., "Retinoic Acid-loaded Polymeric Nanoparticles Induce Neuroprotection in a Mouse Model for Parkinson's Disease", Frontiers in Aging Neuroscience, vol. 7. Available online at: https://doi.org/10.3389/fnagi.2015.00020, Mar. 6, 2015, pp. 1-10.

Fereshtehnejad et al., "Clinical Criteria for Subtyping Parkinson's Disease: Biomarkers and Longitudinal Progression", Brain: a Journal of Neurology, vol. 140, No. 7, Jul. 1, 2017, pp. 1959-1976.

Flavin et al., "Endocytic Vesicle Rupture is a Conserved Mechanism of Cellular Invasion by Amyloid Proteins", Acta Neuropathologica, vol. 134, No. 4, Oct. 2017, pp. 629-653.

Goldstein et al., "Cytochrome C is Released in a Single Step During Apoptosis", Apr. 18, 2005, 10 pages.

González-Liz_e,acu a_ee rraga et al., "Repurposing Doxycycline for Synucleinopathies: Remodelling of α-synuclein Oligomers Towards Non-toxic Parallel Beta-sheet Structured Species", Scientific Reports, vol. 7, Feb. 3, 2017, pp. 1-13.

Gonzalez-Polo et al., "The Apoptosis/Autophagy Paradox: Autophagic Vacuolization Before Apoptotic Death", Journal of Cell Science, vol. 118, No. 14, Jul. 2005, pp. 3091-3102.

Gustot et al., "Amyloid Fibrils are the Molecular Trigger of Inflammation in Parkinson's Disease", Biochemical Journal, vol. 471, No. 3, Nov. 1, 2015, pp. 323-333.

Hinz et al., "Parkinson's Disease: Carbidopa, Nausea, and Dyskinesia", Clinical Pharmacology: Advances and Applications, vol. 6. Available online at: 10.2147/CPAA. S72234., Nov. 2014, pp. 189-194.

Hoyer et al., "Dependence of a-Synuclein Aggregate Morphology on Solution Conditions", Journal of Molecular Biology, vol. 322, No. 2, 2002, pp. 383-393.

Hsu et al., "Alpha-synuclein Promotes Mitochondrial Deficit and Oxidative Stress", The American Journal of Pathology, vol. 157, No. 2. Available online at: 10.1016/s0002-9440(10)64553-1., Aug. 2000, pp. 401-410.

Kahana et al., "Liposome-Based Targeting of Dopamine to the Brain: A Novel Approach for the Treatment of Parkinson's Disease", Molecular Psychiatry, vol. 26, No. 6, May 5, 2020, pp. 2626-2632.

Kavanagh, "Dilution Methods of Antibiotic Assays", Analytical Microbiology, 1963, pp. 125-140.

Kaylor et al., "Characterization of Oligomeric Intermediates in a-Synuclein Fibrillation: FRET Studies of Y125W/Y133F/Y136F a-Synuclein", Journal of Molecular Biology, vol. 353, No. 2, Oct. 21, 2005, pp. 357-372.

Kondrasheva et al., "The Application of L-dopa-containing Polymeric Nanoparticles Provides Motor Function Recovery in 6-ohda-indused Parkinson's Disease Model", Journal of the Neurological Sciences, vol. 333, No. 1. Available online at: 10.1016/j.jns.2013.07.608., Oct. 2013.

Levine, "Quantification of β-sheet Amyloid Fibril Structures with Thioflavin T", Methods in Enzymology, vol. 309, 1999, pp. 274-284.

Levine, "Thioflavine T Interaction with Synthetic Alzheimer's Disease B-amyloid Peptides: Detection of Amyloid Aggregation in Solution", Protein Science, vol. 3, No. 2, 1993, pp. 404-410.

Lewitt, "Levodopa Therapy for Parkinson's Disease: Pharmacokinetics and Pharmacodynamics", Movement Disorders: Official Journal of the Movement Disorder Society, vol. 30, No. 1, Jan. 2015, pp. 64-72.

Morimoto et al., "The Life of Proteins: the Good, the Mostly Good and the Ugly", Nature Structural & Molecular Biology, vol. 18, No. 1, Jan. 2011, 5 pages.

Mossmann, Rapid Colorimetric Assay for Cellular Growth and Survival: Application to Proliferation and Cytotoxicity Assays, Journal of Immunological Methods, Dec. 1983, vol. 65, Nos. 1-2, pp. 55-63.

Murphy, "Peptide Aggregation in Neurodegenerative Disease", Annual Review of Biomedical Engineering, vol. 4. Available online at: https://doi.org/10.1146/annurev.bioeng.4.092801.094202., Aug. 2002, pp. 155-174.

Nakamura, "α-Synuclein and Mitochondria: Partners in Crime?", Neurotherapeutics. vol. 10, No. 3., Available online at: 10.1007/s13311-013-0182-9., Jul. 2013, pp. 391-399.

Nishino et al., "Identification of the Lipopolysaccharide Modifications Controlled by the Salmonella PmrA/PmrB System Mediating Resistance to Fe(III) and Al(III)", Molecular Microbiology, vol. 61, No. 3, Aug. 2006, pp. 645-654.

Ortega et al., "Lipid Nanoparticles for the Transport of Drugs Like Dopamine Through the Blood-Brain Barrier", Beilstein Archives. Available online at: https://doi.org/10.3762/bxiv.2020.79.v1., Jul. 2, 2020, pp. 1-54.

Picconi et al., "Motor Complications in Parkinson's Disease: Striatal Molecular and Electrophysiological Mechanisms of Dyskinesias", Movement Disorders: Official Journal of the Movement Disorder Society, vol. 33, No. 6, Jul. 2018, pp. 867-876.

Pomares et al., "Protective Action of ppGpp in Microcin J25-Sensitive Strains", Journal of Bacteriology, vol. 190, No. 12, Jun. 2008, pp. 4328-4334.

Pukass et al., "Oxidative Stress Promotes Uptake, Accumulation, and Oligomerization of Extracellular Alpha-Synuclein in Oligodendrocytes", Journal of Molecular Neuroscience, vol. 52, No. 3. Available online at: 10.1007/s12031-013-0154-x., Mar. 2014, pp. 339-352.

Reichmann et al., "Ergoline and Non-Ergoline Derivatives in the Treatment of Parkinson's Disease", Journal of Neurology, vol. 253, Available Online at: 10.1007/s00415-006-4009-z., Aug. 2006, 4 pages.

Rinne et al., "Levodopa Alone and in Combination with a Peripheral Decarboxylase Inhibitor Benserazide (Madopar) in the Treatment of

(56) References Cited

OTHER PUBLICATIONS

Parkinson's Disease: a Controlled Clinical Trial", Journal of Neurology, vol. 211, No. 1, Dec. 2, 1975, pp. 1-9.

Santa-Cecília et al., "The Neuroprotective Effect of Doxycycline on Neurodegenerative Diseases", Neurotoxicity Research, Harwood Academic Publishers, Lausanne, Switzerland, vol. 35, No. 4, Feb. 23, 2019, pp. 981-986.

Scott et al., "A Pathologic Cascade Leading to Synaptic Dysfunction in Alpha-Synuclein-Induced Neurodegeneration", The Journal of Neuroscience: The Official Journal of the Society for Neuroscience, vol. 30. No. 24, Jun. 1, 2010, pp. 8083-8095.

Socias et al., "Exploiting the Therapeutic Potential of Ready-to-use Drugs: Repurposing Antibiotics Against Amyloid Aggregation in Neurodegenerative Diseases", Progress in Neurobiology, vol. 162., Mar. 2018, pp. 17-36.

Spillantini et al., "Alpha-synuclein in Lewy Bodies", Nature, vol. 388, No. 6645, Aug. 28, 1997, pp. 839-840.

Stefani et al., "Protein Aggregation and Aggregate Toxicity: New Insights into Protein Folding, Misfolding Diseases and Biological Evolution", Journal of Molecular Medicine, vol. 81, No. 11, Aug. 27, 2003, pp. 678-699.

Tapeinos et al., "Advances in the Design of Solid Lipid Nanoparticles and Nanostructured Lipid Carriers for Targeting Brain Diseases", Journal of Controlled Release: Official Journal of the Controlled Release Society, vol. 264, Oct. 28, 2017, pp. 306-332.

Tsai et al., "Oral Apomorphine Delivery from Solid Lipid Nanoparticles With Different Monostearate Emulsifiers: Pharmacokinetic and Behavioral Evaluations", Journal of Pharmaceutical Sciences, vol. 100, No. 2, Feb. 2011, pp. 547-557.

Wallings et al., "Lysosomal Dysfunction at the Centre of Parkinson's Disease and Frontotemporal Dementia/Amyotrophic Lateral Sclerosis", Trends in Neurosciences, vol. 42, No. 12, Dec. 2019, pp. 899-912.

Xu et al., "Dopamine as a Robust Anchor to Immobilize Functional Molecules on the Iron Oxide Shell of Magnetic Nanoparticles", Journal of the American Chemical Society, vol. 126, No. 32, Jul. 27, 2004, pp. 9938-9939.

Zhao et al., "Luminescent ZnO Quantum Dots for Sensitive and Selective Detection of Dopamine", Talanta, vol. 107, Mar. 30, 2013, pp. 133-139.

Zhu et al., "Dendrimer-Based Drug Delivery Systems for Brain Targeting", Biomolecules, vol. 9, No. 12. Available online at: 10.3390/biom9120790., Nov. 2019, 29 pages.

CHEMICALLY COUPLED TRANSPORTER FOR LOW-HYDROPHOBICITY BIOACTIVE DRUGS INTO THE CENTRAL NERVOUS SYSTEM

PRIOR RELATED APPLICATIONS

This application is a continuation of International Patent Application No. PCT/IB2022/050920, filed on Feb. 2, 2022, which claims the benefit of U.S. Provisional Application No. 63/145,190, filed on Feb. 3, 2021, both of which are hereby incorporated in their entireties by this reference.

FIELD OF THE INVENTION

The present invention relates, in general, to chemically coupled compounds useful as drug-carriers. More particularly, the present invention refers to such compounds for the treatment of neurodegenerative diseases. Specifically, the present invention refers to a compound comprising a modified tetracycline derivative covalently coupled, through a linker, to a low-hydrophobicity bioactive molecule useful for treating neurodegenerative diseases. Yet more specifically, the drug-carrier compound disclosed herein has proven useful and efficient in experimental models of neurodegenerative diseases in vitro, in particular for Parkinson's disease (PD).

BACKGROUND OF THE INVENTION

Neurodegenerative diseases are a heterogeneous group of disorders characterized by progressive loss of selectively vulnerable populations of neurons of the central or peripheral nervous systems. Since the main risk factor for suffering neurodegenerative diseases is age, the increase in longevity in the human population situates these maladies as a critical challenge to health care systems throughout developed countries. In fact, according to a systematic study performed only on Alzheimer's disease, 7.7 million people are affected in the US alone, and this number is estimated to rise to 13.5 million by 2050. Additionally, the actual expenditure for dementia care in the UK almost matches the combined cost of cancer, heart disease and stroke. This highlights the urgent need for effective neuroprotective therapies in order to avoid the collapse of healthcare systems in the near future.

Despite presenting differences in clinical manifestations, different neurodegenerative disorders share many similarities on a sub-cellular level, including protein amyloid aggregation (Stefani M, Dobson C M. *Protein aggregation and aggregate toxicity: new insights into protein folding, misfolding diseases and biological evolution.* J Mol Med. 2003; 81(11):678-99; Murphy R M. *Peptide aggregation in neurodegenerative disease.* Annu Rev Biomed Eng. 2002; 4:155-74; Duda J E, Lee V M, Trojanowski J Q. *Neuropathology of synuclein aggregates.* J Neurosci Res. 2000; 61(2):121-7), neuroinflammation (A, Gallea J I, Sarroukh R, Celej M S, Ruysschaert J M, Raussens V. *Amyloid fibrils are the molecular trigger of inflammation in Parkinson's disease.* Biochem J. 2015; 471(3):323-33. doi: 10.1042/1BJ20150617), oxidative stress (Pukass K, Richter-Landsberg C. *Oxidative stress promotes uptake, accumulation, and oligomerization of extracellular alpha-synuclein in oligodendrocytes.* J Mol Neurosci. 2014; 52(3):339-52. doi: 10.1007/s12031-013-0154-x; Bieschke J, Zhang Q, Powers E T, Lerner R A, Kelly J W. *Oxidative metabolites accelerate Alzheimer's amyloidogenesis by a two-step mechanism, eliminating the requirement for nucleation.* Biochemistry. 2005; 44(13):4977-83) and mitochondrial dysfunction (Nakamura K. *alpha-Synuclein and mitochondria: partners in crime?* Neurotherapeutics. 2013; 10(3):391-9. doi: 10.1007/s13311-013-0182-9; Hsu L J, Sagara Y, Arroyo A, Rockenstein E, Sisk A, Mallory M, et al. *alpha-synuclein promotes mitochondrial deficit and oxidative stress.* Am J Pathol. 2000; 157(2):401-10. Epub 2000 Aug. 10. doi: 10.1016/s0002-9440(10)64553-1), and lysosomal dysregulation (Wallings R L, Humble S W, Ward M E, Wade-Martins R. *Lysosomal Dysfunction at the Centre of Parkinson's Disease and Frontotemporal Dementia/Amyotrophic Lateral Sclerosis.* Trends Neurosci. 2019 December; 42(12):899-912. doi: 10.1016/j.tins.2019.10.002. Epub 2019 Nov. 5. PMID: 31704179; PMCID: PMC6931156).

An ideal treatment should directly target the underlying disease pathogeneses as the primary method of altering the inexorably progressive clinical course of these diseases. It is widely accepted that aggregation of specific proteins is not only a common molecular characteristic, but also a likely trigger for subsequent neuroinflammation, oxidative stress, lysosomal dysregulation, and mitochondrial dysfunction. Furthermore, all these events seem to be linked in a neurotoxic positive feedback loop. Therefore, the inhibition of abnormal protein aggregation should be a main target of therapies for amyloid-associated diseases. Unfortunately, despite the significant investment in research and drug development, to date all attempts have failed.

Although promising compounds have demonstrated an ability to stop or revert protein aggregation in vitro or in animal models, unfortunately most of them failed in clinical trials. Moreover, most drugs currently described as neuroprotective in clinical trial registration databases that reach phase three are mainly aimed at neurotransmitter release regulation or metabolism instead of the inhibition of the abnormal protein aggregation processes (https://clinicaltrials.gov). Therefore, available approaches are more palliative than curative.

Therapeutic approaches to treat neurodegenerative diseases are often limited due to the protective nature of the blood-brain barrier (BBB), which hinders drug targeting towards neurons. The BBB acts as an organic barrier between circulating blood and the central nervous system (CNS), and controls homeostasis, movement of molecules and ions, regulation of influx and efflux transport, and acts as a protective covering that prevents harmful substances from penetrating into the brain. This complex barrier also controls and limits the systemic delivery of therapeutics towards the CNS. The highly selective permeable BBB constitutes the greatest impediment for delivering drugs via blood circulation to treat brain disorders.

Belonging to the group of neurodegenerative diseases, the following may be mentioned: Alzheimer's disease (AD) and other dementias, Parkinson's disease (PD) and PD-related disorders, prion disease, motor neuron diseases (MND), Huntington's disease (HD), spinocerebellar ataxia (SCA), spinal muscular atrophy (SMA).

Among the above mentioned, PD is the second most-spread neurodegenerative disorders, affects 7-10 million people worldwide, and is characterized by motor symptoms and a progressive loss of midbrain dopaminergic neurons (Collaborators GPsD. *Global, regional, and national burden of Parkinson's disease, 1990-2016: a systematic analysis for the Global Burden of Disease Study* 2016. Lancet Neurol. 2018; 17(11):939-53. Epub 2018 Oct. 1. doi: 10.1016/S1474-4422(18)30295-3; Fereshtehnejad S M, Zeighami Y, Dagher A, Postuma R B. *Clinical criteria for subtyping Parkinson's disease: biomarkers and longitudinal progres-* sion. Brain. 2017:140(7):1959-76. doi: 10.1093/brain/awx118). Available pharmacological interventions for PD, such as levodopa and dopamine agonists, ameliorate motor symptoms. However, these treatments lose their efficacy over time and cause adverse side effects (Picconi B, Hernández LF, Obeso J A, Calabresi P. *Motor complications in Parkinson's disease: Striatal molecular and electrophysiological mechanisms of dyskinesias*. Mov Disord. 2018; 33(6):867-76. Epub 2017 Dec. 8. doi: 10.1002/mds.27261). In this context, there is an imperative need to develop disease-modifying therapies in order to prevent or delay disease progression.

Although the molecular basis of neurodegeneration in PD remains controversial, the central role of α-synuclein (AS) amyloid aggregation in the initiation and dissemination of the pathology seems clear (Spillantini M G, Schmidt M L, Lee V M, Trojanowski J Q, Jakes R, Goedert M. *Alpha-synuclein in Lewy bodies*. Nature. 1997; 388(6645):839-40. Epub 1997 Aug. 28. doi: 10.1038/42166; Araki K, Yagi N, Aoyama K, Choong C J, Hayakawa H, Fujimura H, et al. *Parkinson's disease is a type of amyloidosis featuring accumulation of amyloid fibrils of alpha-synuclein*. Proc Natl Acad Sci USA. 2019; 116(36):17963-9. Epub 2019 Aug. 21. doi: 10.1073/pnas.1906124116). Oligomeric AS species have been shown to elicit toxic effects by different mechanisms, such as alteration of membrane permeability with concomitant calcium influx (Danzer K M, Haasen D, Karow A R, Moussaud S, Habeck M, Giese A, et al. *Different species of alpha-synuclein oligomers induce calcium influx and seeding*. J Neurosci. 2007; 27(34):9220-32. doi: 10.1523/JNEUROSCI.2617-07.2007), mitochondrial damage (Hsu L J et al.), lysosomal leakage (Nishino K, Hsu F F, Turk J, Cromie M J, Wosten M M, Groisman E A. *Identification of the lipopolysaccharide modifications controlled by the Salmonella PmrA/PmrB system mediating resistance to Fe(III) and Al(III)*. Mol Microbiol. 2006; 61(3):645-54.), microtubule disruption (Alim M A, Ma Q L, Takeda K, Aizawa T, Matsubara M, Nakamura M, et al. *Demonstration of a role for alpha-synuclein as a functional microtubule-associated protein*. J Alzheimers Dis. 2004; 6(4):435-42; discussion 43-9. Epub 2004 Sep. 4), and interference with axonal transport (Scott D A, Tabarean I, Tang Y, Cartier A, Masliah E, Roy S. *A pathologic cascade leading to synaptic dysfunction in alpha-synuclein-induced neurodegeneration*. J Neurosci. 2010; 30(24):8083-95. Epub 2010 Jun. 18. doi: 10.1523/JNEUROSCI.1091-10.2010). Fibrillar species, on the other hand, provoke neurotoxicity mainly by triggering inflammatory processes (Dos-Santos-Pereira M, Acuña L, Hamadat S, Rocca J, González-Lizárraga F, Chehin R, et al. *Microglial glutamate release evoked by α-synuclein aggregates is prevented by dopamine*. Glia. 2018; 66(11):2353-65), but also by catalyzing their own propagation (Bousset L, Pieri L, Ruiz-Arlandis G, Gath J, Jensen P H, Habenstein B, et al. *Structural and functional characterization of two alpha-synuclein strains*. Nat Commun. 2013; 4:2575. doi: 10.1038/ncomms3575), destabilizing proteostasis networks (Morimoto R I, Driessen A J, Hegde R S, Langer T. *The life of proteins: the good, the mostly good and the ugly*. Nat Struct Mol Biol. 2011; 18(1):1-4. doi: 10.1038/nsmb0111-1), and affecting integrity of cytosolic organelles (Flavin W P, Bousset L, Green Z C, Chu Y, Skarpathiotis S, Chaney M J, et al. *Endocytic vesicle rupture is a conserved mechanism of cellular invasion by amyloid proteins*. Acta Neuropathol. 2017; 134(4):629-53. Epub 2017 May 19. doi: 10.1007/s00401-017-1722-x). Considering that oxidative stress and pro-inflammatory cytokines also promote the toxic aggregation of AS (Pukass K et al.), all these processes are suggested to integrate a vicious cycle that results in neuronal death, with subsequent spreading of toxic species into neighboring healthy neurons (Gonzalez-Lizarraga F, Socias S B, Avila C L, Torres-Bugeau C M, Barbosa L R, Binolfi A, et al. *Repurposing doxycycline for synucleinopathies: remodelling of alpha-synuclein oligomers towards non-toxic parallel beta-sheet structured species*. Sci Rep. 2017; 7:41755. Epub 2017 Feb. 6. doi: 10.1038/srep41755). Thus, to efficiently modify the course of neurodegeneration in PD, an ideal drug should be capable of interfering with AS aggregation, halting the generation of toxic species, disassembling preformed toxic aggregates, and inhibiting neuroinflammatory processes. In addition, such a multi-target compound should also possess the ability to cross the BBB, often an essential obstacle in the pharmaceutical development of medications targeting the central nervous system. Administration of dopamine per se could make up for the lack of this neurotransmitter, but this molecule is too polar to cross the BBB. For this reason, since 1960, the most effective and widespread dopamine replacement therapy is the delivery of its precursor, Levodopa (L-Dopa or L-3,4-dihydroxyphenylalanine) (LeWitt P A. *Levodopa therapy for Parkinson's disease: Pharmacokinetics and pharmacodynamics*. Mov Disord. 2015; 30(1):64-72. Epub 2014 Dec. 3. doi: 10.1002/mds.26082). This amino acid can only modestly cross the BBB using the large amino acid transporters LAT-1 and, once in the CNS, is decarboxylated to become dopamine. It is important to note that dopamine has no transporter reported to date and is too polar a compound to be soluble in lipids and diffuse through the BBB.

In 1975, peripheral decarboxylase inhibitors such as carbidopa or benserazide began to be added to L-Dopa formulations, reducing the dose of L-Dopa necessary to reach the CNS (Rinne U K, Birket-Smith E, Dupont E, Hansen E, Hyyppä M, Marttila R, et al. *Levodopa alone and in combination with a peripheral decarboxylase inhibitor benserazide (Madopar) in the treatment of Parkinson's disease: A controlled clinical trial*. J Neurol. 1975; 211(1):1-9. doi: 10.1007/BF00312459). These formulations were able to control important side effects such as nausea and vomiting. However, the prolonged use of L-Dopa combined with carbidopa brought along new side effects such as dyskinesias, depression, orthostatic hypotension, drowsiness, psychosis, and increased risk behaviors (Hinz M, Stein A, Cole T. *Parkinson's disease: carbidopa, nausea, and dyskinesia*. Clin Pharmacol. 2014; 6:189-94. Epub 2014 Dec. 9. doi: 10.2147/CPAA.S72234). To date, there is no other approved mode of administration available to mitigate the lack of dopamine in the nigrostriatal pathway of the CNS.

The delivery of therapeutical agents to the CNS can be classified into the following categories:

1—Unstructured systems: the conventional way of supplying dopamine to the CNS is through a formulation comprising Levodopa+Carbidopa or benserazide. However, there are several side effects derived from the prolonged use of L-Dopa+carbidopa. Studies of the etiology and adverse effects demonstrated that carbidopa was the drug responsible for said side effects since it causes an irreversible binding and inactivation of vitamin B6 throughout the body. This elicits vast consequences, for it interferes with more than 300 functions of enzymes and proteins (Hinz M et al.). In addition, alterations of thought including the appearance of hallucinations and delusions are associated with the release of dopamine in the mesolimbic or mesocortical system (Rinne U K et al.).

Dopamine agonists (DA) are an effective alternative to Levodopa, mainly for young patients, and are associated with a lower incidence of motor complications after 5 years. They are useful both in monotherapy in the early stages of the disease, and in association with Levodopa in patients with advanced PD. Ergot derivatives were the first available DAs, but their use is currently restricted due to the risk of cardiac valvular fibrosis.

Nowadays non-ergot DA are mostly used. These can be administered orally (pramipexole and ropinirole), transdermally (rotigotine), or subcutaneously (apomorphine). Recently, oral prolonged release presentations have been introduced in the market, which allow a single daily administration of the drug. However, new DAs are not exempted from serious adverse effects (Reichmann H, Bilsing A, Ehret R, Greulich W, Schulz J B, Schwartz A, et al. *Ergoline and non-ergoline derivatives in the treatment of Parkinson's disease*. J Neurol. 2006; 253 Suppl 4:IV36-8. doi: 10.1007/s00415-006-4009-z).

2—Nanostructured Systems:

Nanoparticles of different composition and structure are being studied to transport drugs to the CNS. Generally, these particles are colloidal solids that vary in size between 2 and 100 nm. None of these systems have yet reached the registration or commercial phase, and among them the following can be mentioned:

Dendrimers are arborescent three-dimensional polymers of polymeric species from polyamides (PAMAM), polypropyl-1-amine (DAB-dendr-NH2), polyethers, polyesters, polyalkanes, polyphenylenes, polyphenylacetylenes, etc. The drug may be encapsulated within the dendrimer, or it may be covalently bound to its surface. The dendrimer penetrates the BBB through receptor-mediated endocytosis. While encapsulation of drugs in dendrimers is a very promising strategy, there is no systematic evaluation of dendrimer toxicokinetics with respect to its adsorption, distribution, metabolism, and excretion to address safety issues related to long-term clinical use.

As to the knowledge of the present inventors, there is no disclosure in the literature to date on the encapsulation of dopamine, or other neuroprotective molecules capable of inhibiting or halting cell death, in dendrimers (Zhu Y, Liu C, Pang Z. *Dendrimer-Based Drug Delivery Systems for Brain Targeting*. Biomolecules. 2019; 9(12). Epub 2019 Nov. 27. doi: 10.3390/biom9120790). Dendrimers have a very low encapsulation efficiency and not known to accumulate in specific regions such as nigrostriatal pathway.

Quantum Dots are fluorescent semiconductor nanoparticles that cross the BBB by transferrin receptor-mediated endocytosis. They are made up of a metallic core and an organic covering. Their brightness, photostability, modifiable size and narrow emission spectrum have turned these nanosystems into a revolutionary technology. Various applications in the CNS have been described, including sensitive and selective dopamine detection (Zhao D, Song H, Hao L, Liu X, Zhang L, Lv Y. *Luminescent ZnO quantum dots for sensitive and selective detection of dopamine*. Talanta. 2013; 107: 133-9. Epub 2013 Jan. 11. doi: 10.1016/j.talanta.2013.01.006). However, to the inventors' knowledge, no carrier function for dopamine of these nanoparticles has been reported to date. Moreover, for long-term treatments, they present intrinsic toxicity, and their biocompatibility has not been fully studied. Their current use is mainly focused on diagnosis.

Liposomes are a type of nanoparticles generally formed by a lipid bilayer, inside which there is a hydrophilic nucleus where the drug is encapsulated. Liposomes are capable of crossing the BBB through receptor-mediated transcytosis. Once inside the CNS, the membrane that surrounds them breaks and it releases its contents. The half-life of liposomes is limited, but increases when its surface is coated with polyethylene glycol (PEG). The lipid bilayer helps to prevent hydrolysis and oxidative degradation of the drug encapsulated therein.

Liposomes have been used to encapsulate apomorphine (a dopamine agonist), managing to improve the distribution of the drug within the CNS. Also, a group recently studied a liposome-based delivery system for targeting dopamine to the brain, which yielded a reduced effective dopamine dose in comparison to standard levodopa administration in mice (Kahana et al. *Liposome-based targeting of dopamine to the brain: a novel approach for the treatment of Parkinson's disease*. Mol Psychiatry. 2020 May 5. doi: 10.1038/s41380-020-0742-4).

As a disadvantage, however, liposomes have poor stability, low encapsulation efficiency, rapid elimination by the reticuloendothelial system, cellular interactions or adsorption, and a high production cost.

Micelles are colloidal particles with a size of 5-100 nm, made up of two parts: a hydrophobic interior and a hydrophilic exterior. Penetration of micelles through the BBB is accomplished by receptor-mediated transcytosis. However, they are not very stable and are extremely sensitive to oxidative processes, limiting their efficiency for transporting substances to the CNS.

To date, there are no research works referring to encapsulation of dopamine or other neuroprotective substances in micelles.

Carbon nanotubes are comprised of an allotropic form of carbon, which consists of one or several sheets of graphene wound on themselves and arranged in a concentric way to form cylinders with a size of 1-50 nm, having particular electrical, mechanical and thermal properties. Carbon nanotubes insert into the BBB and allow the release of the drug. Penetration of carbon nanotubes through the BBB is mainly performed by receptor-mediated endocytosis, although other mechanisms such as diffusion and phagocytosis are also feasible. Although these nanostructures are commercially available, they are severely contaminated with metallic catalysts and amorphous carbons, thereby posing toxicity (due to inflammation), lead to the formation of granulomas, biocompatibility problems, and represent a hazard to both human health and the environment.

As to the knowledge of the present inventors, there are no research works to date referring to encapsulation of dopamine or other neuroprotective substances in carbon nanotubes.

Polymeric nanoparticles have a wide range of sizes between 1-1000 nm. Drugs can be associated with these nanoparticles by adsorption or by covalent bonds that keep them bound to their surface. They are mainly characterized by their good stability. Their penetration into the BBB occurs through receptor-mediated endocytosis. Esteves et al., demonstrated that administration of these nanoparticles with retinoic acid produces a neuroprotective effect on dopaminergic neurons (Esteves M, Cristóväo AC, Saraiva T, Rocha S M, Baltazar G, Ferreira L, et al. *Retinoic acid-loaded polymeric nanoparticles induce neuroprotection in a mouse model for Parkinson's disease*. Front Aging Neurosci. 2015; 7:20. Epub 2015 Mar. 6. doi: 10.3389/fnagi.2015.00020). One of the advantages of using this type of nanoparticles is that their chemistry is well known and there is plenty of information regarding their toxicity.

To date, there is no published research referring to the encapsulation of dopamine or dopamine agonists in polymeric nanoparticles.

Solid lipid nanoparticles are a type of nanoparticles with a size ranging from 100-400 nm, and a matrix composed of lipids that remain in solid state, both at room temperature and at body temperature. They are biodegradable, biocompatible and have low toxicity. They cross the BBB by diffusion. Esposito et al. encapsulated the dopamine agonist Bromocriptine in these nanoparticles (Esposito E, Mariani P, Ravani L, Contado C, Volta M, Bido S, et al. *Nanoparticulate lipid dispersions for bromocriptine delivery: characterization and in vivo study.* Eur J Pharm Biopharm. 2012; 80(2):306-14. Epub 2011 Nov. 9. doi: 10.1016/j.ejpb.2011.10.015). This nasally administered formulation showed a reversal of stiffness in an experimental model of PD in mice.

On the other hand, Tsai et al., formulated apomorphine, a dopamine receptor agonist (DA), in solid lipid nanoparticles, managing to increase oral bioavailability and regional distribution in the brain in animal models (Tsai M J, Huang Y B, Wu P C, Fu Y S, Kao Y R, Fang J Y, et al. *Oral apomorphine delivery from solid lipid nanoparticles with different monostearate emulsifiers: pharmacokinetic and behavioral evaluations.* J Pharm Sci. 2011; 100(2):547-57. Epub 2010 Aug. 27. doi: 10.1002/jps.22285). Kondrasheva et al., have designed a new carrier for L-DOPA consisting of solid lipid nanoparticles with polyacid (lactic-co-glycolic) PLGA that, when administered nasally, provides a long-lasting recovery of motor functions, improving the efficacy of the drug (I. G. Kondrasheva, P. E. Gambaryan, E. S. Severin, A. A. Guseva, A. A. Kamensky. *The application of L-DOPA-containing polymeric nanoparticles provides motor function recovery in 6-OHDA-induced Parkinson's disease model.* Journal of the Neurological Sciences. 2013, Volume 333, Supplement 1, Page e97. https://doi.org/10.1016/j.jns.2013.07.608) Recent research was published relating to the encapsulation of dopamine in solid lipid nanoparticles (Ortega et al. *Lipid nanoparticles for the transport of drugs like dopamine through the blood-brain barrier.* Beilstein Archives. 2020, 202079. https://doi.org/10.3762/bxiv.2020.79.v1; Tapeinos et al. *Advances in the design of solid lipid nanoparticles and nanostructured lipid carriers for targeting brain diseases.* J Control Release. 2017 Oct. 28; 264: 306-332. doi:10.1016/j.jconrel.2017.08.033). The disadvantages of this system consist in the strong tendency towards gelatinization of the vesicles and the low efficiency of incorporation of the drug. Furthermore, the availability of pure lipids and the degree of conservation that the preparation requires make this system unfeasible for scaling-up and ensuring provisions for permanent and long-term treatments.

There is still a need to develop stable, inexpensive, and reliable transport methods for allowing hydrophilic drugs to be transferred through the BBB towards their intended targets at the CNS.

SUMMARY OF THE INVENTION

According to a first aspect, the present invention provides a new compound comprising a modified tetracycline derivative, covalently coupled through a linker to a low-hydrophobicity bioactive molecule useful for treating neurodegenerative diseases.

A second aspect of the present invention is to provide a pharmaceutical composition comprising the compound of the invention, and one or more pharmaceutically acceptable excipients.

A third aspect of the present invention is to provide a method for treating a neurodegenerative disease comprising administering a therapeutically effective amount of the compound of the invention to a subject in need thereof.

A fourth aspect of the present invention is to provide a use of the compound according to the invention, for manufacturing a medicament for the treatment of a neurodegenerative disease.

A fifth aspect of the present invention is to provide a method for preparing a compound according to the invention.

BRIEF DESCRIPTION OF THE DRAWINGS

The following figures form part of the present specification and are included to further illustrate certain aspects of the present invention.

DETAILED DESCRIPTION OF THE INVENTION

The present invention refers to a new compound based on a structural modification carried out on a tetracycline derivative which is covalently coupled to a low-hydrophobicity bioactive molecule useful for treating neurodegenerative diseases via a linker.

The compound disclosed herein is useful as a carrier or transporter for bioactive substances into the central nervous system. The present inventors have found that this drug-carrier compound can cross the BBB and as such is useful in the therapy of neurodegenerative diseases, such as Parkinson's disease (PD).

The proof of concept (POC) of the coupling system disclosed herein was carried out using dopamine as the molecule to be transported. However, as any person of skill in the art will appreciate, the invention may apply to any low-hydrophobicity bioactive molecule useful for treating neurodegenerative diseases. As previously mentioned herein, dopamine needs to be introduced into the CNS in neurodegenerative pathologies such as PD, but its polarity limits its access to the brain. After applying the chemical coupling procedure described herein, the resulting transporter molecule substantially increased the XlogP of free dopamine, reaching an adequate value to permeate the BBB. The transporter preserves the binding affinity for AS aggregates which is characteristic of doxycycline with possible tropism towards the nigrostriatal region, which could generate in vivo bioaccumulation in the regions affected by neurodegenerative processes where these aggregates are found.

Figure 1:
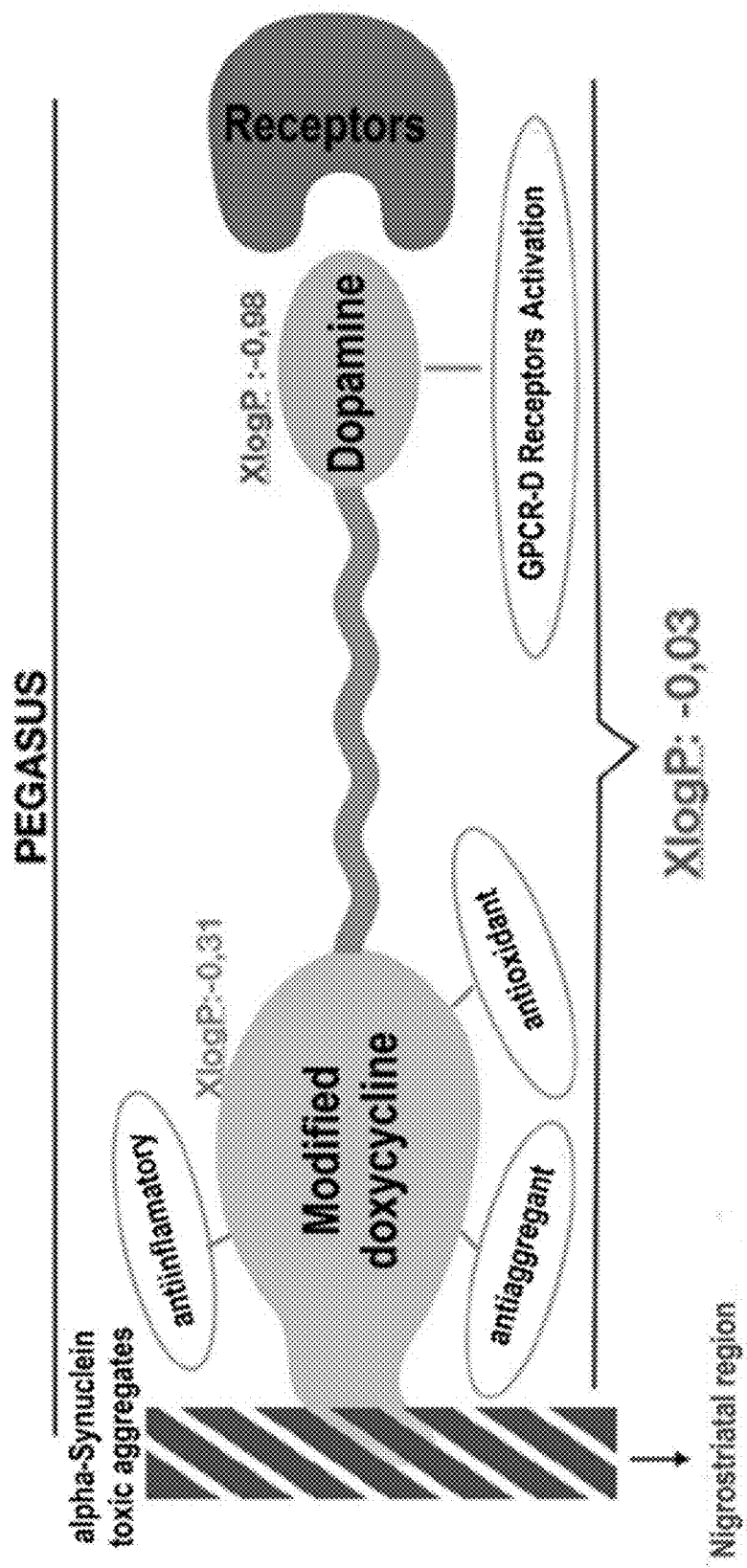
FIG. 1. Representative diagram of one of the compounds of the invention, indicating biological properties and XlogP values for each component thereof, both separately and within the coupled structure.

A representative diagram of the compound of the invention is shown in FIG. 1, indicating biological properties and XlogP values for each component, both separately and within the coupled structure.

The chemically coupled transporter disclosed herein represents a new concept of site-directed drug carrier, capable of simultaneously effecting both a substitution and a neuroprotective therapy.

In this sense, the present invention provides a new alternative for the treatment of neurodegenerative diseases, in particular PD, by means of a novel compound that addresses the drawbacks of currently available therapies for the mentioned clinical conditions.

When designing the synthetic scheme for production of the compound of the invention, the present inventors considered the modification of tetracycline to include the inhibition of unwanted effects such as its antibiotic activity and the addition of a functionalizable linker to easily couple the molecules to be transported. The design of the conjugated compound of the present invention allows the two molecules joined by the linker to properly retain their chemical structures.

Correspondingly, it is an object of this invention to provide a new compound comprising a modified tetracycline derivative, covalently coupled through a linker to a low-hydrophobicity bioactive molecule useful for treating neurodegenerative diseases.

Within the scope of this invention, the term "modified tetracycline derivative" refers to a chemical compound which is structurally related to tetracycline, of formula (I):

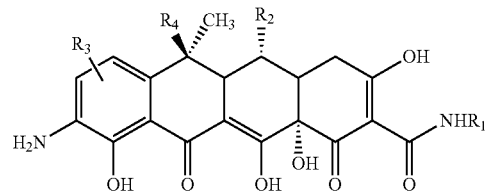

wherein $R_1$ is selected from H, $CH_2NHR$, $CH_2NRR$ and COR;

$R_2$ is selected from H, OH and OCOR;

$R_3$ is selected from H and Cl;

$R_4$ is selected from H and OH; and each R is independently selected from H, alkyl, benzyl, aryl and allyl.

In a preferred embodiment of the invention, the tetracycline derivative is a chemically modified doxycycline derivative. By "chemically modified doxycycline derivative", the present description refers to a compound which is structurally related to doxycycline, which is an antibiotic known in the art.

Most preferably, the tetracycline derivative is the compound named D5 or DOXI-5 by the inventors, wherein $R_1$ is H, $R_2$ is OH, $R_3$ is H and $R_4$ is H, as defined by the following formula:

(D5)

Within the scope of this invention, the term "linker" refers to a small moiety having the property of linking the two coupled structures, acting as a bifunctional connecting element therewithin.

The linker comprised within the compounds of the invention is defined by the generic formula XZX. In a particular embodiment of the invention, the linker is selected from the group consisting of:

X(—$CH_2$—)$_n$X, wherein each X is independently selected from CO and $CH_2$, and n ranges from 0 to 16;

$XCH_2CH_2SSCH_2CH_2X$, wherein each X is independently selected from OCO and HNCO;

wherein X is CO; and

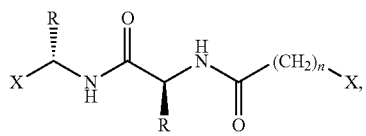

wherein X is CO and R is an amino acid substituent.

In a preferred embodiment, the linker is defined by formula X(—CH$_2$—)$_n$X, wherein n ranges from 0 to 3. In a particularly preferred embodiment, the linker is defined by formula X(—CH$_2$—)$_n$X, wherein X is CO and n is 2.

Within the scope of the present invention, the term "low-hydrophobicity bioactive molecule useful for treating neurodegenerative diseases" refers to a hydrophilic chemical compound exhibiting biological activity at the CNS level upon administration to a subject, which is known to function as a drug for treating neurodegenerative diseases. The low hydrophobicity of such a compound impedes its crossing of the BBB, which prevents it from reaching its intended target at the CNS without either chemical modification of finding a proper carrier system for it.

The low-hydrophobicity bioactive molecule useful for treating neurodegenerative diseases may be selected from a variety of drugs, such as neuroprotectors, antibiotics, antimycotics, antineoplastic drugs, anti-inflammatory drugs, among others.

In a particularly preferred embodiment, the low-hydrophobicity bioactive molecule useful for treating neurodegenerative diseases is dopamine.

In a most preferred embodiment, the compound of the invention comprises dopamine as the low-hydrophobicity bioactive molecule useful for treating neurodegenerative diseases, compound D5 as the tetracycline derivative, and a linker defined by defined by formula X(—CH$_2$—)$_n$X, wherein X is CO and n is 2. In such an embodiment, the compound of the invention is the compound the inventors named Pegasus, defined by the following formula:

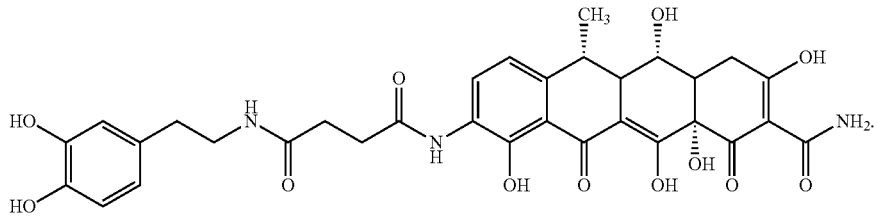

(Pegasus - D9)

The compound is also referred to as D9. The terms "Pegasus" and "D9" are thus used interchangeably throughout this description.

Other advantages of the compound Pegasus of the invention are mentioned below:
- It does not transport the precursor but the bioactive substance directly.
- It does not use amino acid transporters because it has the necessary physicochemical characteristics to cross the BBB.
- It would a priori not need to be administered in combination with decarboxylase inhibitors, avoiding any possible side effect related thereto.
- It appears to retain the neuroprotective effects reported for doxycycline, as observed in in vitro experimental results.

In an embodiment of the invention, the compound according to the invention is intended for use in treating a neurodegenerative disease.

Preferably, the neurodegenerative disease to be treated is a synucleinopathy. The term "synucleinopathy" is to be understood as referring to a neurodegenerative disease characterized by the formation of toxic aggregates of AS in the CNS. Examples of synucleinopathies which may be treated by the compound of the invention are PD, dementia with Lewy bodies (DLB), multiple system atrophy (MSA), neuroaxonal dystrophies and Alzheimers disease with amygdalar restricted Lewy bodies (AD/ALB). In a particularly preferred embodiment, the compound according to the invention is intended for use in treating PD.

The compound of the invention is additionally intended for use in treating other neurodegenerative diseases, such as standard Alzheimer's disease (AD), Huntington's disease, amyotrophic lateral sclerosis, brain tumors, brain infectious disease, among others.

The compound of the invention is intended to be administered to a subject in need thereof by means of its inclusion within a suitable pharmaceutical composition. Therefore, it is another aspect of this invention the provision of a pharmaceutical composition comprising the compound of the invention and one or more pharmaceutically acceptable excipients, so that the compound may be readily administered to the subject.

The pharmaceutical composition of the invention may take several forms known to the person of skill in the art. For example, the pharmaceutical composition may be in a solid oral form such as a tablet or a capsule, a liquid form such as an orally or parenterally administrable solution, among others. The pharmaceutically acceptable excipients may be selected by a person of skill in the art according to the dosage form selected for the pharmaceutical composition, the low-hydrophobicity bioactive molecule useful for treating neurodegenerative diseases to be administered, and the specific neurodegenerative disease to be treated, among other considerations.

As mentioned above, the compound according to the invention is intended for use in treating a neurodegenerative disease. Therefore, it is yet another aspect of the present invention to provide a method for treating a neurodegenerative disease comprising administering a therapeutically effective amount of the compound of the invention to a subject in need thereof. The neurodegenerative disease to be treated may be a synucleinopathy, preferably selected from the group consisting of PD, DLB, MSA, neuroaxonal dystrophies and AD/ALB. Alternatively, the neurodegenerative disease to be treated may be selected from the group consisting of standard Alzheimer's disease (AD), Huntington's disease, amyotrophic lateral sclerosis, brain tumors, and brain infectious disease.

A person of skill in the art will be able to establish the therapeutically effective amount to administer to the subject in view of the disease to be treated and the low-hydrophobicity bioactive molecule useful for treating neurodegenerative diseases to be administered.

In a particularly preferred embodiment, this aspect of the invention relates to a method for treating PD comprising administering a therapeutically effective amount of the compound of the invention to a subject in need thereof.

An additional aspect of the present invention is to provide a use of the compound according to the invention, for manufacturing a medicament for the treatment of a neurodegenerative disease. The neurodegenerative disease to be treated may be a synucleinopathy, preferably selected from the group consisting of PD, DLB, MSA, neuroaxonal dystrophies and AD/ALB. Alternatively, the neurodegenerative disease to be treated may be selected from the group consisting of standard Alzheimer's disease (AD), Huntington's disease, amyotrophic lateral sclerosis, brain tumors, and brain infectious disease.

A person of skill in the art will be able carry out this aspect of this invention, using the compound of the invention for manufacturing the medicament by means of techniques known in the art.

In a particularly preferred embodiment, this aspect of the invention relates to the use of the compound according to the invention, for manufacturing a medicament for the treatment of PD.

Yet another aspect of the present invention is to provide a method for preparing the compound Pegasus according to the invention. The method comprises the following steps:
i) Removal of the dimethylamino function at C-4 of doxycycline.
ii) Introduction of an amino function at C-9 of the deamination product.
iii) Selective protection of the phenolic hydroxyl groups of dopamine (and derivatives) as benzyl ethers.
iv) Introduction of the linker at the amino function of the previous product by reaction with succinic anhydride to give the corresponding amido-acid.
v) Coupling of the acid group of the amido-acid with the amino group of doxycycline via a mixed anhydride to afford the doxycycline-dopamine conjugate, which upon deprotection of the benzyl groups gave the desired compound (Pegasus).

As made evident by the working examples included within this patent application, the method described above leads to the intended compound in a surprising manner, while other tried methods did not succeed in reaching said compound.

The synthetic scheme was designed to carry out suitable chemical modifications to the doxycycline molecule by eliminating its antibiotic activity. This allows the molecule to be used in long-term treatments without generating selective pressure on the microbiota and/or the environment. In addition, it is necessary to add the linker in a region of the molecule that does not interfere with its ability to bind to aggregated species of AS. Based on our previous knowledge of the structure-function relationship of tetracyclines (Socias S B, Gonzalez-Lizarraga F, Avila C L, Vera C, Acuna L, Sepulveda-Diaz J E, et al. *Exploiting the therapeutic potential of ready-to-use drugs: Repurposing antibiotics against amyloid aggregation in neurodegenerative diseases*. Prog Neurobiol. 2018; 162:17-36. Epub 2017 Dec. 16. doi: 10.1016/j.pneurobio.2017.12.002), the linker was located at C9 serving as a bridge to covalently bind at the opposite end to the dopamine molecule. The chemical analysis detailed below demonstrates that the structure of both molecules was preserved throughout the modification/conjugation procedure.

It is also important to highlight that the synthesis strategy used by the present inventors allows for the preservation of important biological properties of the molecules, and that the resulting XlogP (partition coefficient (P) indicating the ratio of concentrations of a compound in a mixture of two immiscible solvents at equilibrium) suggests that the molecule has the hydrophobicity necessary to cross the BBB.

As will be shown in the examples of the present invention, the chemically coupled transporter disclosed herein has also proven to be a non-toxic molecule for dopaminergic cell culture models, retaining beneficial properties for protecting against neurological pathologies, such as antioxidative, anti-aggregation and anti-inflammatory activities.

The compound of the present invention is useful in PD therapy and has shown the following advantages:
a) as a therapeutic strategy in PD and other synucleinopathies, the compound of the invention serves in alleviating dopamine deficiency and interfering in the progression of the disease, since it would have at least two targets: 1) neuronal death process, through its neuroprotective activity derived from the tetracycline portion of the molecule and 2) bioaccumulation of dopamine in the nigrostriatal system activating dopaminergic receptors.
b) it improves the efficiency (as evidenced by an adequate LogP) in the delivery to the CNS of therapeutic compounds in neurological pathologies, for example, chemotherapeutic, antibiotic, antiviral or antioxidant molecules whose administration by other means is not adequate or viable. Indeed, the treatment of disorders such as HIV, dementia, epilepsy, neurogenic pain, meningitis and brain cancers depend mainly on the ability of drugs to achieve a higher concentration in the brain.

Although side effects of the compound of the present invention still need to be studied in clinical trials, the future formulation of the molecule will not need the presence of carbidopa since the invention does not use the precursor L-dopa or the amino acid transport system for getting through to the SNC.

EXAMPLES

The present invention is further illustrated by the following Examples, which are not intended to limit the scope thereof. Instead, the Examples set forth below should be understood only as exemplary embodiments for better taking into practice the present invention.

Example 1—Organic Synthesis of the Compound of the Invention

The design of the synthetic scheme for production of the compound of the invention will be described in detail below.

The present inventors prepared a conjugated chemical entity by attaching two molecules by means of a linker. Thus, the synthesis involved suitable chemical modifications to a doxycycline molecule which was bound to a dopamine derivative through a spacer or linker located within a region not interfering with the tetracycline's ability to bind to aggregated species of AS. As was demonstrated by chemical analysis, the structure of both main coupled molecules was preserved throughout the procedure.

1. Synthesis of Key Intermediate 9-amino-4-dedimethylaminodoxycycline D5

For the synthesis of D5, previously described procedures were followed, to which suitable modifications were introduced (International Application published as WO 2003057169; C. Berens et al. ChemBioChem 2006, 7, 1320-1324; TC Barden et al. J. Med. Chem. 1994, 37, 3205-3211).

The procedure employed required the preparation of doxycycline free form (D1) from commercially available doxycycline hydrochloride (or doxycycline hyclate). This was successfully accomplished by precipitation of D1 from a water solution of the salt, upon addition of a solution of NaOH. The next step was the elimination of the C-4 dimethylamino group of D1 (the numbering of the C atoms of its skeleton is shown in Scheme I below). For this, D1 was treated with excess methyl iodide in THF to give the trimethylammonium salt D2. This compound D2 reacted with Zn(0) in acetic acid to give the deaminated derivative D3.

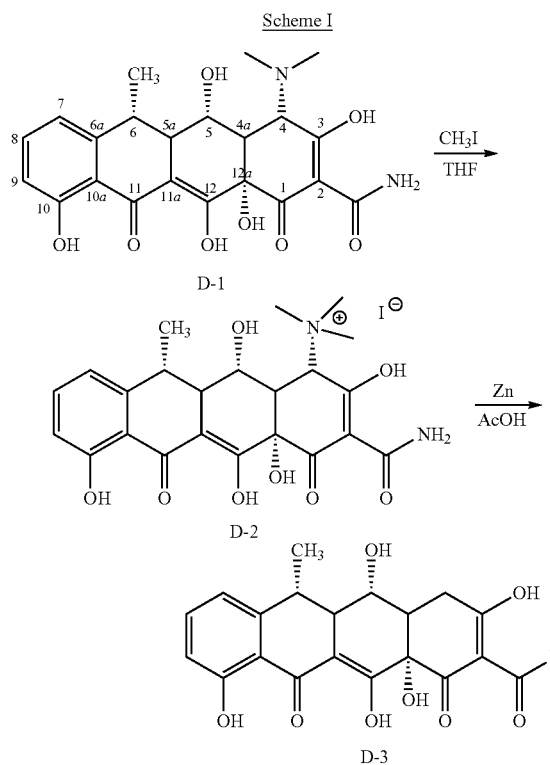

Scheme I

In order to introduce a reactive functionality (an amino group) in the tetracyclic core, nitration of D3 was carried out with potassium nitrate and sulfuric acid to produce the nitro derivative D4. In this process, the isolation and purification protocols of D4 previously described have been modified, and successive precipitations were used to obtain D4 with a good degree of purity. Next, hydrogenolysis of the nitro group of D4 led to the derivative 9-amino-4-dedimethylaminodoxycycline D5. The amino functionality at C-9 is essential to introduce a linker for allowing conjugation of this molecule with dopamine. Nitration and hydrogenolysis steps are shown in Scheme II below.

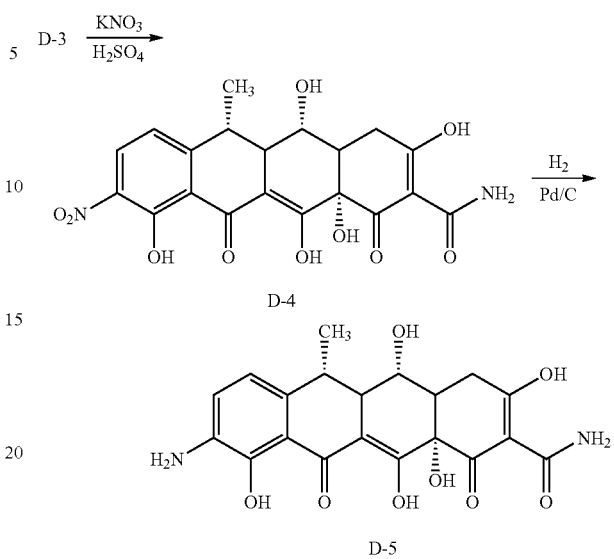

Scheme II

2. Introduction of Spacer (Linker) in D5 or in Dopamine and Formation of Conjugates of Both Units For obtaining a covalent bond between D5 and dopamine the present inventors introduced a bifunctional bonding element (referred to herein as spacer or linker) between these two molecules. 2-Chloroacetyl chloride was first used as a binding agent. This compound reacted with D5 to give intermediate 6, as shown in Scheme III below. The reaction of substitution of the chlorine atom by attack of the amino group of dopamine would lead to the doxycycline-dopamine conjugate. However, the intramolecular attack of the phenolic OH of C-10 occurred, leading to cyclic compound 8.

Unfortunately, all coupling attempts between 6 and dopamine were unsuccessful, under various reaction conditions.

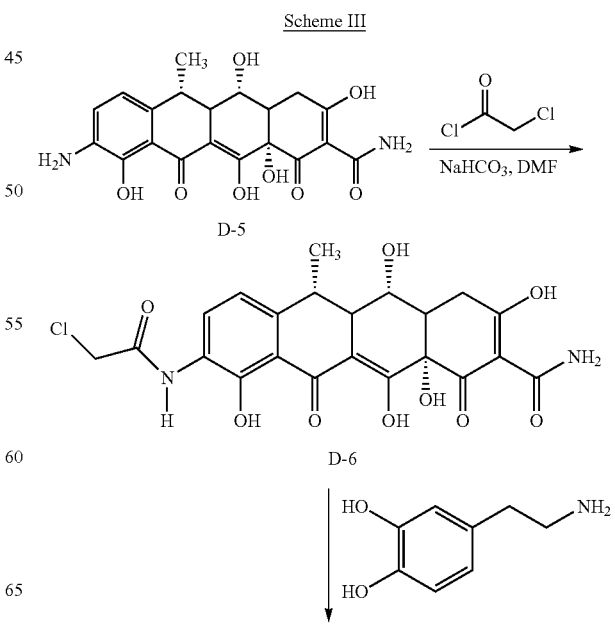

Scheme III

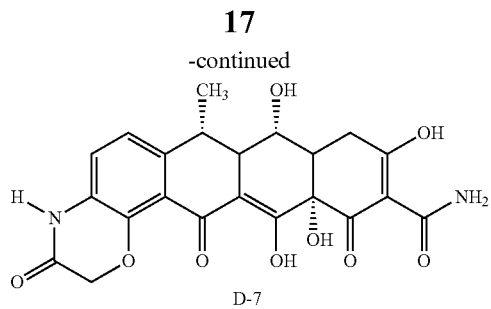

D-7

To verify whether this negative result was the consequence of steric effects due to the proximity of the reactive center containing Cl with the doxycycline nucleus, a halogenated derivative with a longer chain length was introduced. For this, the reaction of D5 with 5-bromovaleric acid was carried out, using DCC as coupling agent. As expected, the amide derivative D8 was obtained, as shown in Scheme IV below. This derivative D8 was characterized by NMR and MS spectroscopy. However, the next step (substitution of Br with dopamine) did not yield satisfactory results either.

Scheme IV

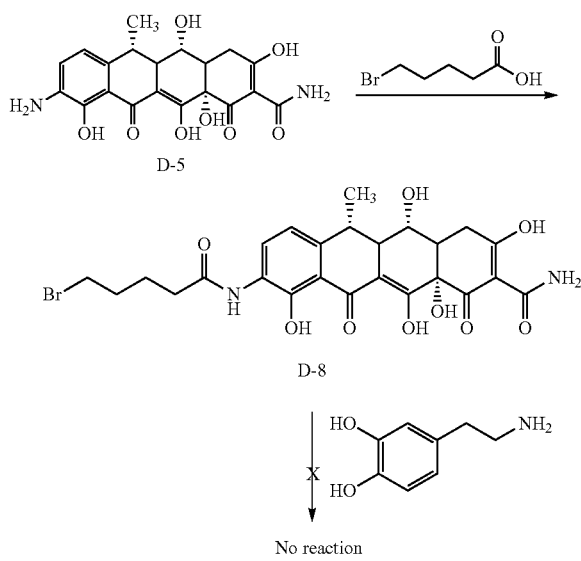

The synthetic strategy was then modified, conducting the reaction of D5 with succinic anhydride, to give the expected product (D9), see Scheme V below. For the amide formation between D9 and dopamine, various condensing agents (DCC, EDCl, HOBt) were used, but no coupling product formation was observed under the several conditions tested.

Scheme V

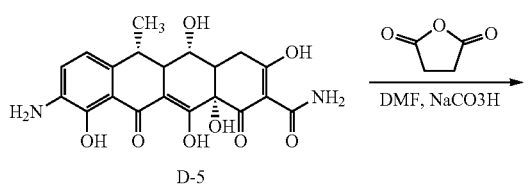

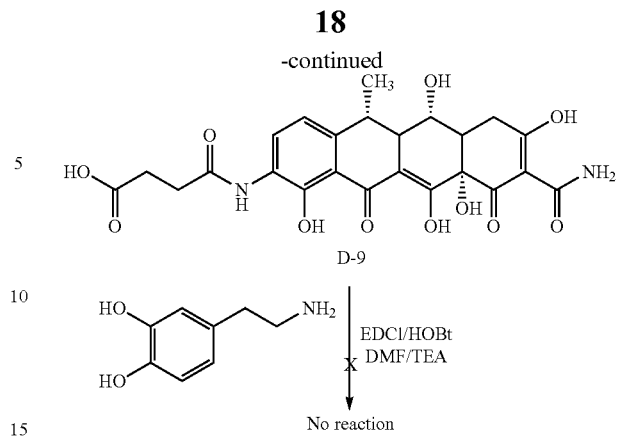

On the other hand, a modification to the reaction order was proposed by adding the succinic anhydride linker to dopamine. This way, the opening of anhydride by the amino group of dopamine led to D10 (see Scheme VI below). Unfortunately, condensation of the carboxylic acid of D10 with the amino of D5, in the presence of the various condensing agents employed, did not produce the expected compound.

Scheme VI

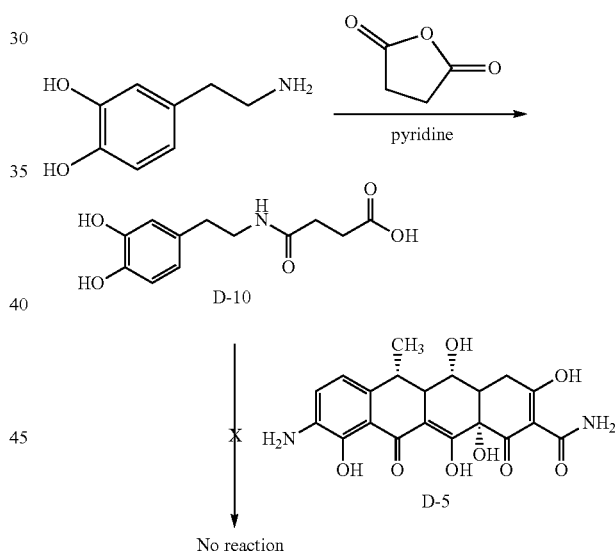

All attempts of coupling reaction between D5 and dopamine were unsuccessful; this could be attributed to the polyfunctionalization of these precursors, which could lead to unwanted interactions or non-selective reactions with other functional groups present in the molecule. For this reason, it was decided to modify the synthetic strategy and try reactions on the O-benzylated derivative of dopamine, which was prepared through the multistep procedure described below.

3. Protection of Phenolic Hydroxyls of Dopamine (and Derivatives) as Benzyl Ethers The phenolic hydroxyl groups of dopamine are nucleophiles that may compete in the reactions of the amino group. To render such phenolic hydroxyl groups inert, they were protected as benzyl ethers. This protection would have the additional advantage of reducing polarity of dopamine, increasing its solubility in organic solvents in which D5 is insoluble (thus, facilitating purification). In addition, the protection could also prevent the generation of strong hydrogen-bond interactions with the D5 functionalities. Benzyl ethers undergo hydrogenolysis in the presence of a catalyst (Pd/C) to regenerate the original hydroxyl groups. To obtain the benzyl ethers, the procedure described by B. Xu et al. (J. Am. Chem. Soc. 2004, 126, 9938-9939) was followed.

Firstly, the amino group of dopamine was protected as the tert-butyloxycarbonyl (BOC) derivative (11), through reaction with di-tert-butyldicarbonate [(BOC)$_2$O] in the presence of NaOH/dioxane. Then, compound 11 was treated with an excess of benzyl bromide/K$_2$CO$_3$ to give di-O-benzyl ether 12. The amino group of 12 was released by hydrolysis of the BOC-carbamate with trifluoroacetic acid, to produce the desired di-O-benzylated derivative 13.

Scheme VII

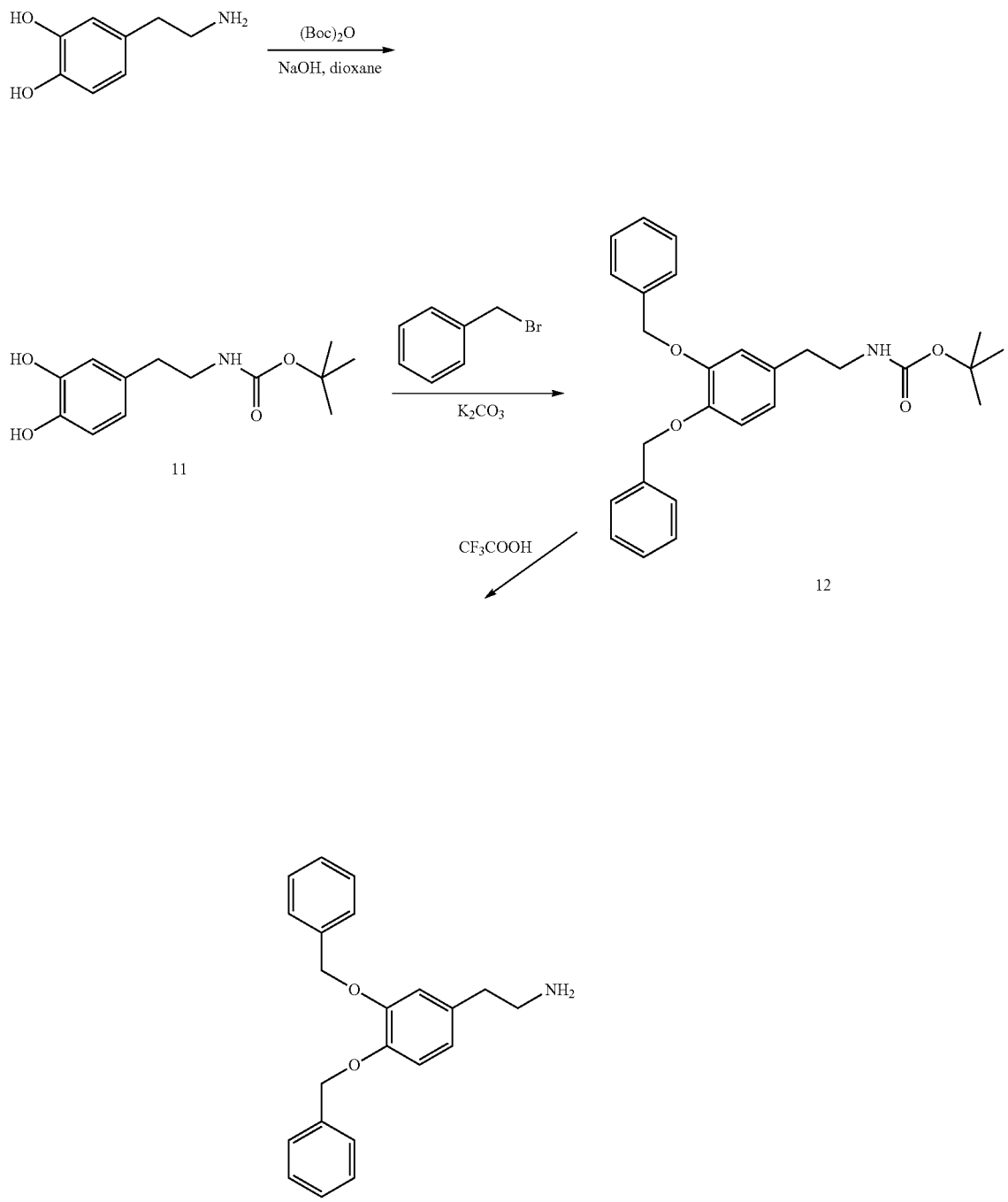

To introduce the linker at 13, the reaction of this compound was conducted with succinic anhydride to successfully give the amido-acid 14. However, the coupling reaction between 14 and D5 in the presence of EDCl/H-OBt, as well as with other coupling reagents, was unsuccessful (see Scheme VIII below).

Scheme VIII

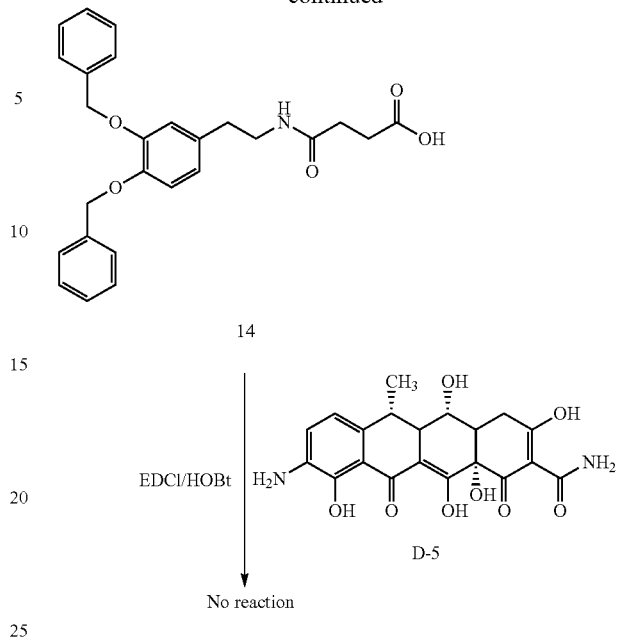

Fortunately, the coupling of 14 with D5, via the mixed anhydride 15 (not isolated) yielded the doxycycline-dopamine conjugate 16 (see Scheme IX) which was more easily isolated and purified. Removal of the benzyl groups of D16 by hydrogenolysis led to the target molecule, i.e., the preferred compound of the invention Pegasus. This product was isolated by precipitation and purified by reverse-phase hplc using methanol:water 30:70 as solvent. The chromatogram recorded in methanol exhibited a single peak having a retention time of 8.4 min.

Scheme IX

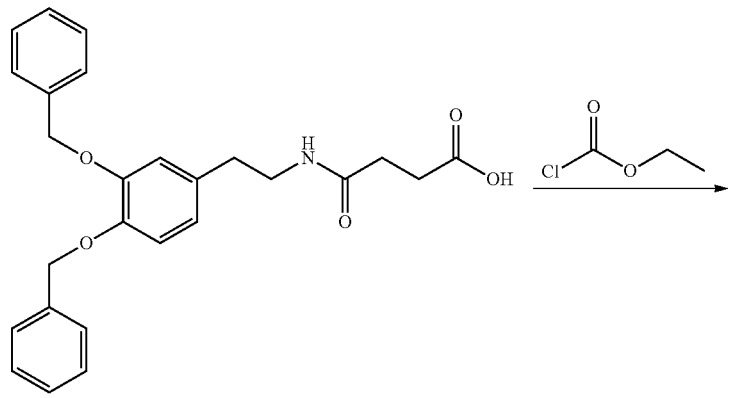

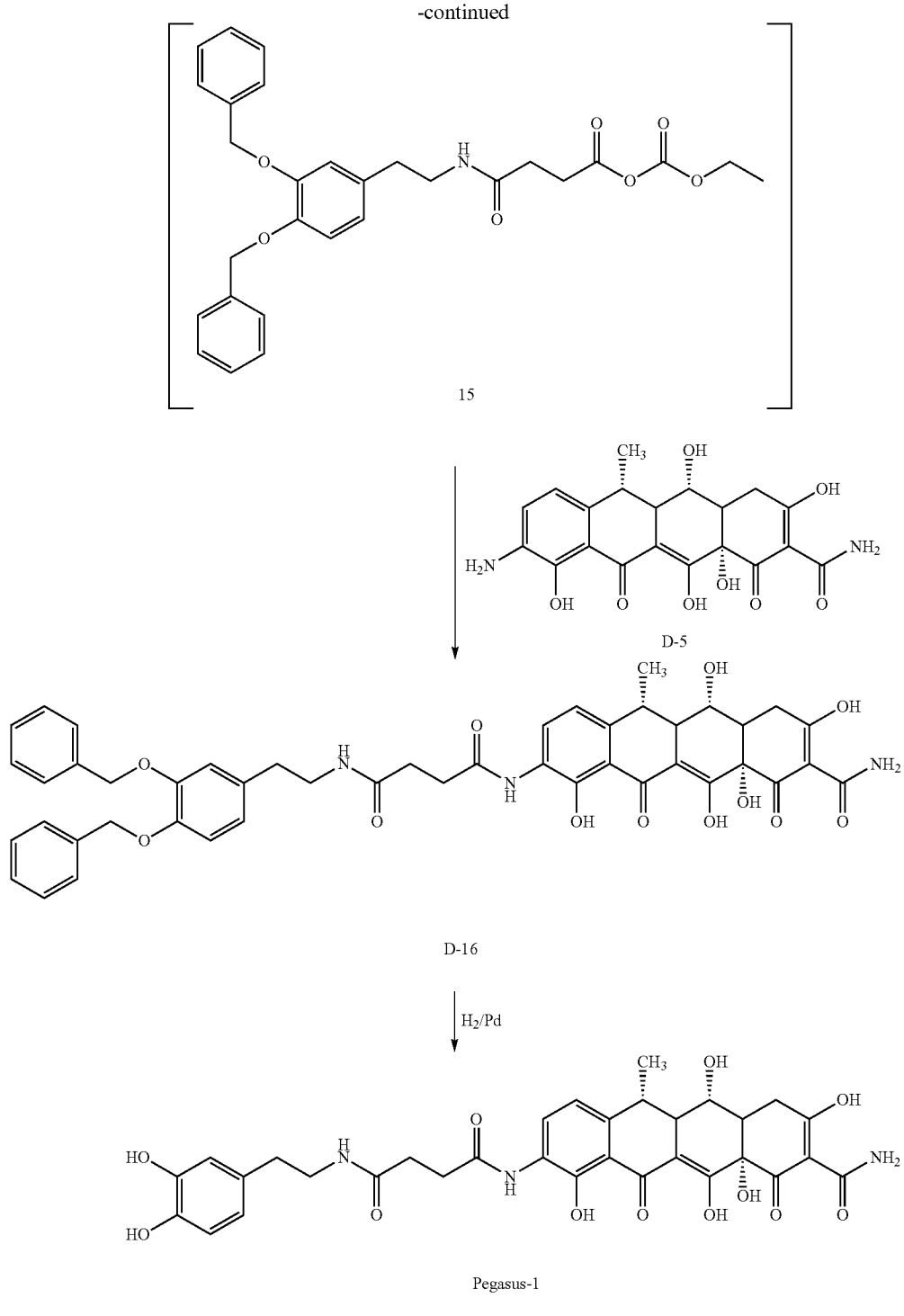

Example 2—Definitive Synthetic Pathway of the Compound Pegasus

General Experimental Procedures

NMR spectra were recorded at 500 MHz ($^1$H) or 125.7 MHz ($^{13}$C) or at 300 MHz ($^1$H) or 75.6 MHz ($^{13}$C). Chemical shifts (δ, in ppm) were referred to an internal standard (Me$_4$Si in CDCl$_3$ (δ 0.0) for $^1$H and CDCl$_3$ (δ: 77.0) for $^{13}$C) or to a residual solvent peak. Data multiplicities are indicated as s (singlet), d (doublet), t (triplet), q (quartet), m (multiplet), br (broad); coupling constants (J) given in Hertz (Hz). Assignments of $^1$H and $^{13}$C NMR spectra were assisted by 2D $^1$H-COSY or NOESY, and 2D $^1$H-$^{13}$C HSQC. High-resolution mass spectra (HRMS) were obtained using the electrospray ionization (ESI) technique and Q-TOF detection. Analytical thin-layer chromatography (TLC) was carried out on silica gel 60 F254 aluminum-supported plates (layer thickness 0.2 mm) and on silica gel 60 RP F254S aluminum-supported plates. The spots were visualized by exposure to UV light and by charring with Ce/Mo stain.

Column chromatography was carried out with silica gel 60 (230-400 mesh) or, for reverse phase, octadecyl-functionalized silica gel was employed as stationary phase. The chromatography solvents or the stepwise solvent polarity gradients used are specified for each individual compound. Optical rotations were measured at the sodium D line at room temperature in a 1 dm cell, in the solvent indicated. Unless otherwise noted, all commercially available compounds were used as obtained from suppliers without further purification.

Doxycycline Free Form (D1) from Doxycycline Hydrochloride

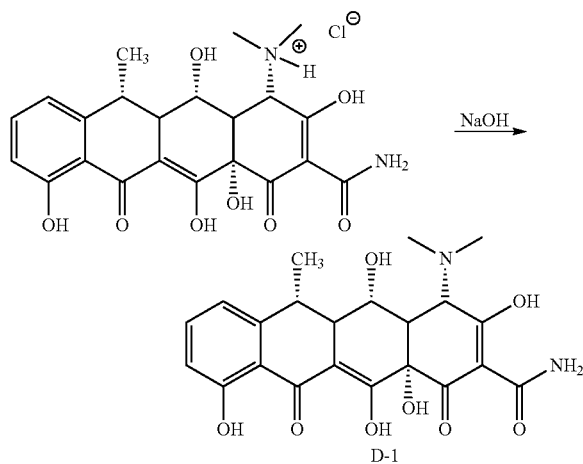

Doxycycline hydrochloride (2.0 g, $[\alpha]_D^{20}$=−113.5 (c 1, 10 mM HCL in MeOH) was dissolved in distilled water (6 mL) and 1 M aqueous NaOH was added dropwise up to pH≈5. At this point a white solid was formed. The solid was filtered and dissolved in methanol (20 mL). The solution was stirred for 20 min until a new white precipitate appeared. The solid was filtered and dried, affording doxycycline free form (D1, 1.3 g, 75%); $[\alpha]_D^{20}$=+250.7 (c 1, THF), $^1$H NMR ((CD$_3$)$_2$CO, 500 MHz) δ: 7.53 (t, 1H, $J_{7,8}$=$J_{8,9}$ 8.1 Hz, H-8), 7.02 (d, 1H, $J_{8,9}$=8.1 Hz, H-9), 6.82 (d, 1H, $J_{7,8}$=8.1 Hz, H-7), 4.21 (brt, 1H, $J_{5a,5}$≈$J_{4a,5}$≈4.0 Hz, H-5), 3.59 (brd, 1H, $J_{4a,4}$=9.6 Hz, H-4), 2.93 (dq, 1H, $J_{6,Me}$=6.7, $J_{5a,6}$=12.8 Hz, H-6), 2.74 (dd, 1H, $J_{5a,5}$=4.0, $J_{5a,6}$=12.8 Hz, H-5a), 2.63 (dd, 1H, $J_{4a,4}$=9.6, $J_{4a,5}$=4.0 Hz, H-4a), 2.53 (s, 6H, N(CH$_3$)$_2$), 1.61 (d, 3H, $J_{6,Me}$=6.7 Hz, CH$_3$); $^{13}$C NMR ((CD$_3$)$_2$CO, 125.7 MHz) δ: 194.7 (C-1,3,11), 174.9, 174.5 (C-12, CONH$_2$), 163.4 (C-10), 148.7 (C-6a), 137.6 (C-8), 117.4, 116.8, 116.4 (C-7,9,10a), 106.4 (C-11a), 92.0 (C-2), 76.0 (C-12a), 69.9 (C-5), 66.2 (C-4), 48.9 (C-4a), 48.2 (C-5a), 42.6 (N(CH$_3$)$_2$), 38.5 (C-6), 16.7 (CH$_3$).

This same procedure was applied to doxycycline hyclate yielding 69% of pure D1.

Synthesis of Doxycycline Methyl Iodide Salt (D2)

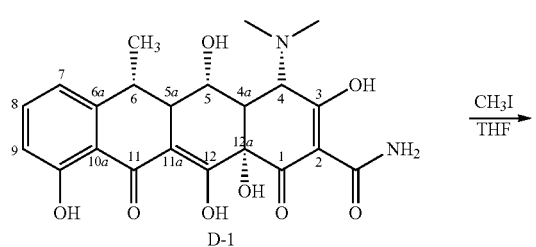

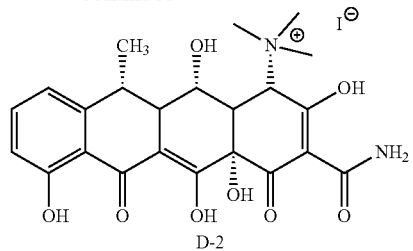

To a solution of D1 (2.0 g, 4.5 mmol) in dry THF (40 mL) was added dropwise methyl iodide (2.5 mL, 40 mmol) at room temperature and under Ar atmosphere. The reaction was stirred at 45° C. for 24 h, and the solvent was removed by evaporation under reduced pressure. The resulting solid was washed with anhydrous CH$_2$Cl$_2$ (15 mL) and dried to give D2 (2.6 g, 98%). $[\alpha]_D^{20}$+31.2 (c 1.0, THF); $^1$H NMR ((CD$_3$)$_2$CO, 200 MHz) δ: 7.55 (t, 1H, $J_{7,8}$=$J_{8,9}$=8.0 Hz, H-8), 6.97 (d, 1H, $J_{8,9}$≈8.0 Hz, H-7), 6.86 (d, 1H, $J_{7,8}$≈8.1 Hz, H-9), 5.44 (s, 1H, OH), 3.89 (brt, 1H, H-5), 3.69 (s, 9H, N(CH$_3$)$_3$), 3.53 (brd, 1H, H-4), 2.97-2.60 (m, 3H, H-4a,5a, 6), 1.56 (d, 3H, $J_{6,Me}$=6.4 Hz, CH$_3$); HRMS (ESI) m/z [M]$^+$ calcd for C$_{23}$H$_{27}$N$_2$O$_5$ 459.1762, found 459.1762.

Synthesis of 4-Dedimethylaminodoxycycline D3

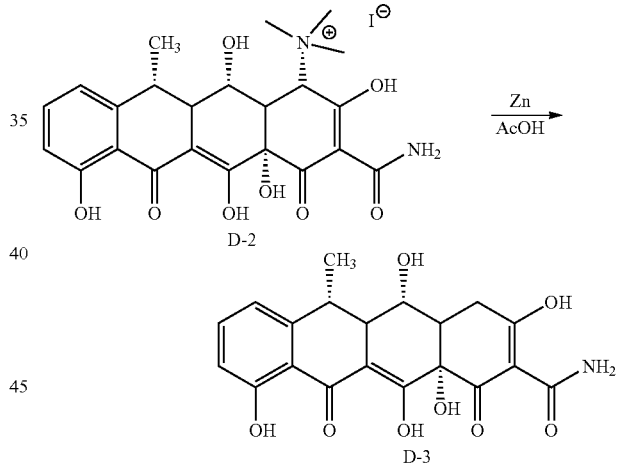

To a solution of D2 (1 g, 1.7 mmol) in 50% (v/v) aqueous acetic acid (30 ml) was added zinc dust (0.6 g, 9.2 mmol) and the mixture was stirred at room temperature for 20 min. The suspension was filtered through a pad of celite. The filtrate was diluted with water (100 mL) containing concentrated HCl (1 mL) and this mixture was stirred in an ice bath for 1 h. The solid formed was filtered and dried in vacuum. This amorphous solid was characterized as D3 (0.48 g, 70%); $[\alpha]_D^{20}$ −50.8 (c 1.0, acetone); $^1$H NMR ((CD$_3$)$_2$CO, 500 MHz) δ: 7.51 (t, 1H, $J_{7,8}$=$J_{8,9}$=8.0 Hz, H-8), 6.96 (d, 1H, $J_{8,9}$=8.0 Hz, H-9), 6.84 (d, 1H, $J_{7,8}$=8.0 Hz, H-7), 4.41 (d, 1H, $J_{5,OH}$=8.5 Hz, OH), 3.79 (br q, 1H, $J_{4a,5}$=9.5, $J_{5a,5}$=7.7, $J_{5,OH}$=8.5 Hz, H-5), 3.06 (dd, 1H, $J_{4a,4}$=5.5, $J_{4,4'}$=18.6 Hz, H-4), 2.97 (dd, 1H, $J_{4a,4'}$=2.9, $J_{4,4'}$=18.6 Hz, H-4'), 2.79 (m, 1H, $J_{6,Me}$=6.8, $J_{5a,6}$=12.5 Hz, H-6), 2.51 (dd, 1H, $J_{5a,5}$=7.7, $J_{5a,6}$=12.5 Hz, H-5a), 2.47 (ddd, 1H, $J_{4a,4}$=5.5, $J_{4a,4'}$=2.9, $J_{4a,5}$=9.5 Hz, H-4a), 1.57 (d, 3H, $J_{6,Me}$=6.8 Hz, CH$_3$); $^{13}$C NMR ((CD$_3$)$_2$CO, 125.7 MHz) δ:195.9, 194.6, 193.2 (C-1, 3,11), 176.0, 174.9 (C-12, CONH2), 163.1 (C-10), 149.1 (C-6a), 137.4 (C-8), 116.8, 116.7, 116.6 (C-7,9,10a), 107.4 (C-11a), 99.7 (C-2), 75.7 (C-12a), 69.6 (C-5), 44.4 (C-4a), 47.6 (C-5a), 39.5 (C-6), 30.6 (C-4), 16.4 (CH$_3$); HRMS (ESI) m/z [M+Na]$^+$ calcd for C$_{20}$H$_{19}$NNaO$_8$ 424.0998, found 424.1003.

Synthesis of 4-dedimethylamino-9-nitro Doxycycline D4

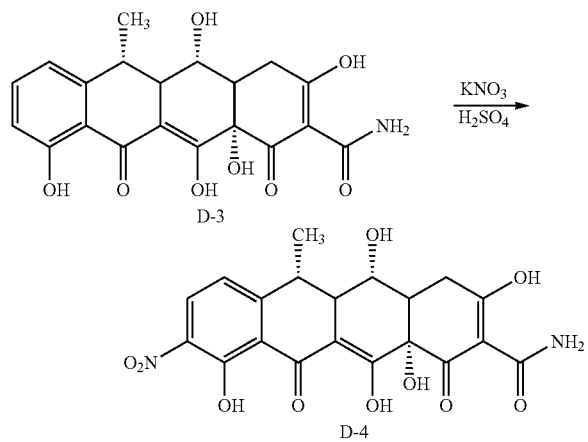

To D3 (0.5 g, 1.2 mmol) was slowly added 97% H$_2$SO$_4$ (4 mL). which had been previously cooled in an ice bath. To this solution KNO$_3$ (0.16 g, 1.6 mmol) was added and the mixture was stirred at 0° C. for 2 h. The reaction was diluted with cold methanol (5 mL) and upon addition of water (35 mL) a precipitate was formed. The brownish solid was filtered, dried in vacuum and then dissolved in acetone (4 mL). Upon addition of dichloromethane (15 mL) a black precipitate appeared. This mixture was treated with activated carbon with stirring for 20 min, and then filtered through a celite pad. The solid was discarded and the filtrate was slowly diluted with hexane (70 mL) to induced the precipitation of D4 (0.35 g, 65%) as a yellow solid; [α]$_D^{20}$ −6.5 (c 1.0, acetone); $^1$H NMR ((CD$_3$)$_2$CO, 200 MHz) δ: 8.15 (d, 1H, J$_{7,8}$=8.6 Hz, H-8), 7.17 (d, 1H, J$_{7,8}$=8.6 Hz, H-7), 3.83 (dd, 1H, J$_{4a,5}$=11.4, J$_{5a,5}$=7.8 Hz, H-5), 3.00-2.91 (m, 3H, H-4H-4' and H-6), 2.61 (dd, 1H, J$_{5a,5}$=12.5, J$_{5a,5}$=7.8 Hz, H-5a), 2.47 (ddd, 1H, J$_{4a,4}$=5.3, J$_{4a,4'}$=3.3, J$_{4a,5}$=11.4 Hz, H-4a), 1.60 (d, 3H, J$_{6,Me}$=6.8 Hz, CH$_3$); $^{13}$C NMR ((CD$_3$)$_2$CO, 50.3 MHz) δ: 165.5 (C-12, CONH$_2$), 155.1 (C-7), 137.4 (C-6a), 132.1 (C-9), 118.5, 118.2 (C-9,10a) 116.5 (C-8), 107.5 (C-11a), 94.6 (C-2), 75.6 (C-12a), 69.2 (C-5), 46.6 (C-5a), 44.2 (C-4a), 38.8 (C-6), 33.4 (C-4), 16.2 (CH$_3$); HRMS (ESI) m/z [M+Na]$^+$ calcd for C$_{20}$H$_{18}$N$_2$NaO$_{10}$ 469.0854, found 469.0854

Synthesis of 9-Amino-4-Dedimethylamino Doxycycline D5

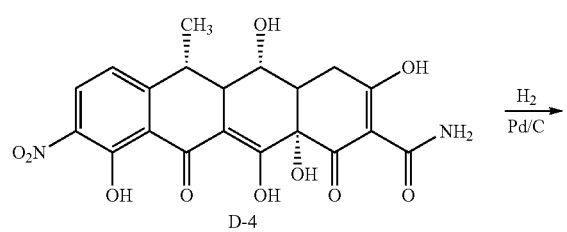

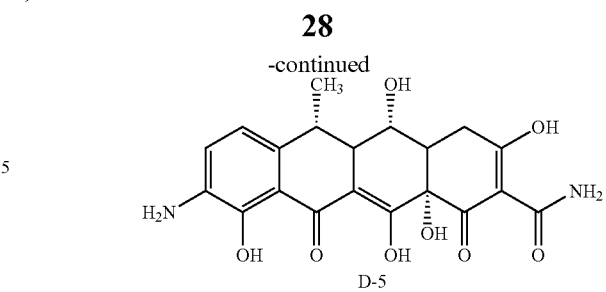

To a solution of D4 (0.2 g, 0.5 mmol) in methanol (6 mL) containing 0.1% concentrated HCl was added 10% Pd/C (30 mg) and the mixture was treated with hydrogen at 44 psi and room temperature for 20 h. The mixture was filtered through a celite pad and the residue washed with methanol. The filtrate and washing liquors were pooled and concentrated. The resulting residue was dissolved in ethanol (2 mL) and precipitation was induced upon dropwise addition of ethyl acetate (30 mL), to afford D5 (125 mg, 60%) as a slightly grey solid; [α]$_D^{20}$ −30.0 (c 0.5, MeOH); $^1$H NMR (CD$_3$OD, 500 MHz) δ: 7.61 (d, 1H, J$_{7,8}$=8.3 Hz, H-8), 7.10 (d, 1H, J$_{7,8}$=8.3 Hz, H-7), 3.67 (dd, 1H, J$_{4a,5}$=10.8, J$_{5a,5}$=8.0 Hz, H-5), 3.05 (dd, 1H, J$_{4a,4}$=5.5, J$_{4,4'}$=18.6 Hz, H-4), 2.92 (dd, 1H, J$_{4a,4'}$=2.4, J$_{4,4'}$=18.6 Hz, H-4'), 2.78 (m, 1H, J$_{6,Me}$=6.9, J$_{5a,6}$=12.4 Hz, H-6), 2.44 (dd, 1H, J$_{5a,5}$=8.0, J$_{5a,6}$=12.4 Hz, H-5a), 2.32 (ddd, 1H, J$_{4a,4}$=5.5, J$_{4a,4'}$=2.4, J$_{4a,5}$=10.8 Hz, H-4a), 1.55 (d, 3H, J$_{6,Me}$=6.9 Hz, CH$_3$); $^{13}$C NMR (CD$_3$OD, 125.7 MHz) δ: 196.5, 194.5×2 (C-1,3,11), 177.2, 175.04 (CONH$_2$, C-12), 155.8 (C-10), 150.4 (C-6a), 130.9 (C-8), 118.9, 118.1 (C-9,10a) 117.3 (C-7), 108.0 (C-11a), 99.5 (C-2), 76.0 (C-12a), 69.8 (C-5), 47.7 (C-5a), 44.9 (C-4a), 40.0 (C-6), 31.3 (C-4), 16.2 (CH$_3$); HRMS (ESI) m/z [M]$^+$ calcd for C$_{20}$H$_{21}$N$_2$O$_8$ 417.1292; found 417.1295.

Synthesis of 9-(2-chloroacetamido)-4-dedimethylamino doxycycline D6

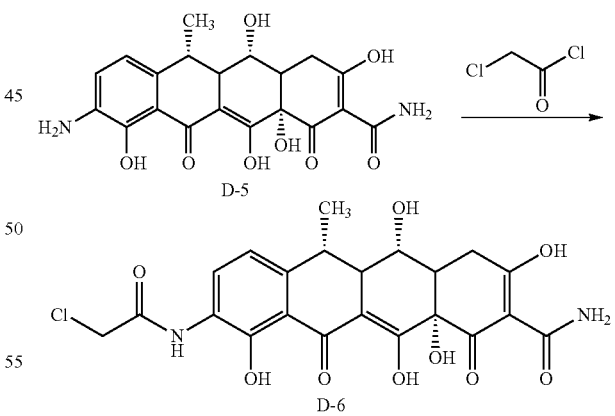

In a dark bottom flask, D5 (125 mg, 0.30 mmol) was dissolved in anhydrous DMF (1.5 mL) and chloroacetyl chloride (25 μL, 0.3 mmol) and NaHCO$_3$ (73 mg, 0.90 mmol) were added. The mixture was stirred at room temperature for 30 min, when an additional amount of the chloroacetyl chloride (19 μL, 0.2 mmol) and NaHCO$_3$ (36 mg, 0.40 mmol) were added. The mixture was stirred for 2 h at room temperature, and the reaction was finished by evaporation of DMF. Addition of methanol to the residue led to the formation of a black precipitate that was filtered and discarded. Water was added to the methanolic solution leading to formation of a brownish solid, which was dried and identified as D6 (54 mg, 36%); $^1$H NMR ((CD$_3$)$_2$SO, 200 MHz); 8.13 (d, 1H, J$_{7,8}$=8.2 Hz, H-8), 6.92 (d, 1H, J$_{7,8}$=8.3 Hz, H-7), 4.41 (s, 2H, CH$_2$Cl), 3.45 (m, 1H, H-5), 2.95 (m, 2H, H-4, H-4'), 2.50-2.43 (m, 2H, H-4a, 5 overlapped with DMSO), 1.42 (d, 3H, J$_{6,Me}$=6.3 Hz, CH$_3$).

Synthesis of the Pentacyclic Derivative D7

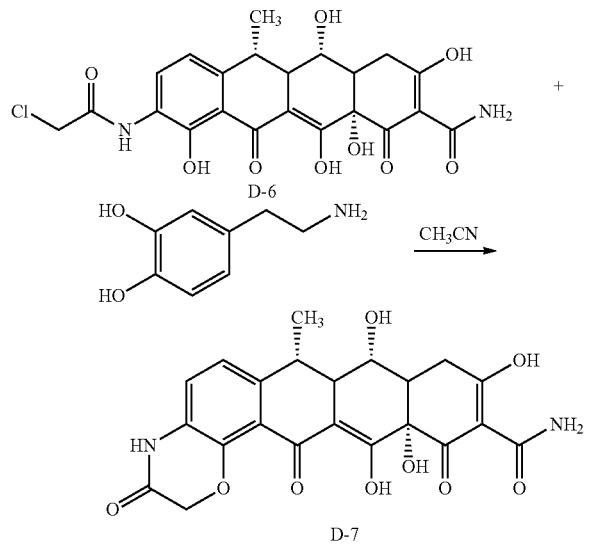

In a round bottom flask with a magnetic bar D6 (24 mg, 0.03 mmol) was dissolved in anhydrous CH$_3$CN (0.7 mL). Then, dopamine (0.03 mmol) was added, and the reaction was purged with nitrogen and stirred at 50° C. for 15 h. Evaporation of the solvent led to a rather complex mixture of products, according to silicagel TLC (EtOAc: C$_5$H$_5$N: H$_2$O 9:2.5:1). Precipitation from water led to a small amount of a solid (7 mg), enriched in a product identified as D7. The contaminant was unreacted D6. Diagnostics signals for D7: $^1$H NMR ((CD$_3$)$_2$CO, 200 MHz); 8.45 (d, 1H, J$_{7,8}$=8.5 Hz, H-8), 6.96 (d, 1H, J$_{7,8}$=8.5 Hz, H-7), 4.67 (d, 1H, J=5.2 Hz, COCH$_2$O), 4.60 (d, 1H, J=5.2 Hz, COCH$_2$O), 3.45 (m, 1H, H-5), 1.52 (d, 3H, J$_{6,Me}$=6.9 Hz, CH$_3$). The singlet observed at 4.67 ppm suggested the formation of the cyclic product by intramolecular nucleophilic attack of the HO-phenol to the halogenated carbon, with displacement of chloride.

Synthesis of 9-(5-bromopentanamido)-D5 (D8) and Attempted Reaction with Dopamine

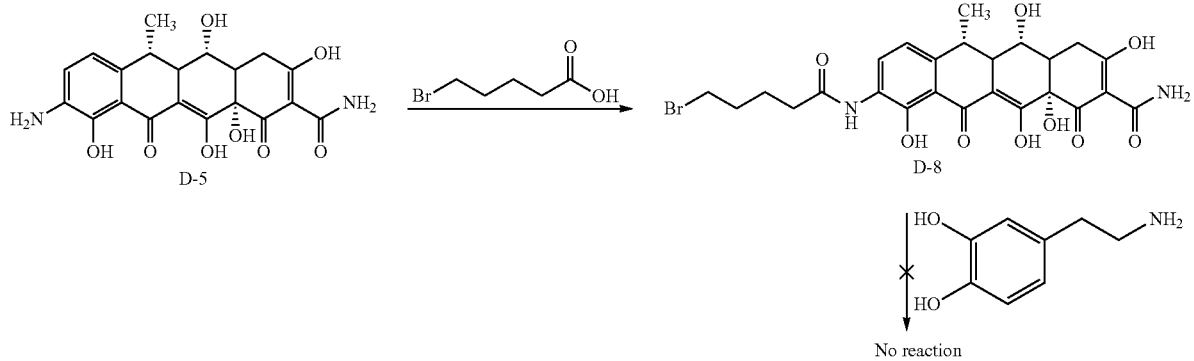

To a solution of 5-bromovaleric acid (325 mg, 1.8 mmol) in anhydrous dichloromethane (9 mL), cooled to 0° C., was added dropwise a solution of DCC (185 mg, 0.9 mmol) in anhydrous dichloromethane (1.8 mL). The reaction was stirred for 30 min at 0° C. and then cooled to −18° C. (ice/salt bath) and stirred for 1 h. After this time, the precipitate of the urea byproduct was filtered and discarded. The organic solution was concentrated to afford the symmetric anhydride from 5-bromovaleric acid, which was reserved for the next step.

In another round bottom flask, D5 (100 mg, 0.24 mmol) was dissolved in dry DMF (3.0 mL) and stirred at room temperature, while the DMF solution of 5-bromovaleric anhydride was added. Upon addition of sodium bicarbonate (0.04 g, 0.5 mmol) the reaction mixture was stirred for 3 h. Examination by reverse phase TLC (H$_2$O:MeOH 1:1) showed the formation of a new spot of Rf 0.31. The mixture was filtered to remove the excess of NaHCO$_3$ and acidified to pH 2 with concentrated, aqueous HCl. The solvent was removed by evaporation and the residue dissolved in MeOH. Addition of water induced the precipitation of D8 (90 mg, 50%).

$^1$H NMR (CDCl$_3$, 300 MHz); 8.53 (d, 1H, J$_{7,8}$=8.5 Hz, H-8), 6.89 (d, 1H, J$_{7,8}$=8.5 Hz, H-7), 3.77 (m, 1H, H-5), 3.45 (m, 3H, CH$_2$Br), 1.60 (d, 3H, J$_{6,Me}$=5.3 Hz, CH$_3$); the $^{13}$C NMR ((CD$_3$)$_2$CO, 125.7 MHz) of the product exhibited the signals of the valeric acid amide residue at 34.4, 33.0, 24.9, and 24.2 ppm.

HRMS (ESI) m/z [M+Na]$^+$ calcd for C$_{25}$H$_{28}$N$_2$BrO$_9$ 579.0973, found 579.0971 and 581.0941 (isotopic pattern 1:1).

As in the case of compound D6, and under analogous conditions, the attempted substitution of the bromide of D8 by dopamine was unsuccessful.

Synthesis of D9, by Addition of D5 with Succinic Anhydride, and Attempted Coupling of D9 with Dopamine

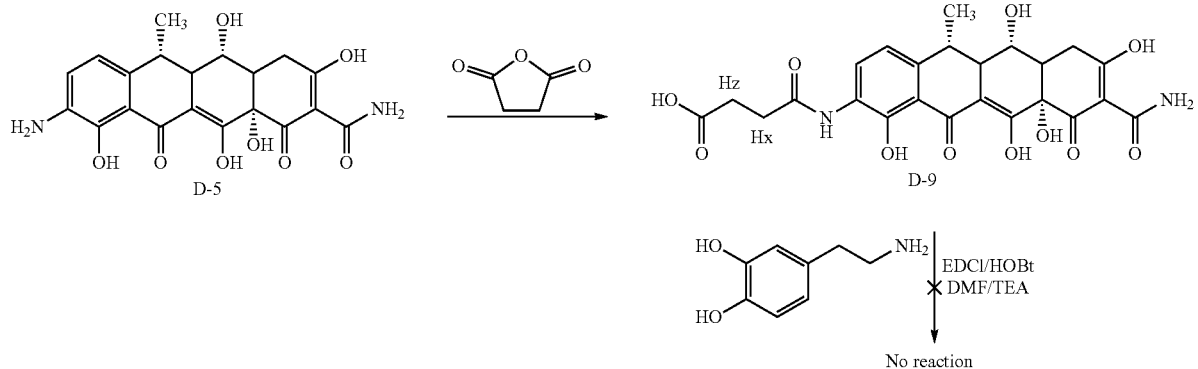

A solution of D5 (0.2 g, 0.5 mmol) in dry DMF (2 mL) was stirred at room temperature while succinic anhydride (81 mg, 1.0 mmol) and sodium bicarbonate (0.08 g, 1.0 mmol) were successively added. The reaction was stirred for 2 h, when examination by reverse phase TLC ($H_2O$:MeCN 7:3) showed the formation of a new spot of Rf 0.34. The crude mixture was filtered to remove the excess of $NaHCO_3$ and acidified to pH 2 with concentrated HCl. The solvent was removed by evaporation. Purification by reverse phase column chromatography ($H_2O$:MeCN 7:3) afforded D9 (150 mg, 60%); $^1$H NMR ($(CD_3)_2CO$, 500 MHz); 8.46 (d, 1H, $J_{7,8}$=8.3 Hz, H-8), 6.90 (d, 1H, $J_{7,8}$=8.3 Hz, H-7), 3.79 (t, 1H, $J_{4a,5}$=$J_{5a,5}$=10.2 Hz, H-5), 3.05 (dd, 1H, $J_{4a,4}$=5.5, $J_{4,4'}$=18.7 Hz, H-4), 2.96 (dd, 1H, $J_{4a,4'}$=3.2, $J_{4,4'}$=18.7 Hz, H-4'), 2.81 (t, 2H, $J_{x,z}$=6.6 Hz, H-Z), 2.70 (t, 2H, $J_{x,z}$=6.6 Hz, H-X), 2.70 (H-6 overlapped under H-X), 2.50-2.43 (m, 2H, H-4a, 5), 1.54 (d, 3H, $J_{6,Me}$=6.8 Hz, $CH_3$); $^{13}$C NMR ($(CD_3)_2CO$, 125.7 MHz) δ: 195.9, 194.6, 193.1 (C-1,3,11), 176.3, 174.9, 174.2, 171.3 (CONH2, COOH, C-12, CONH), 152.1 (C-10), 142.6 (C-6a), 127.3, 127.2 (C-8, 9), 116.0, 115.8 (C-7, 10a), 107.4 (C-11a), 99.7 (C-2), 75.7 (C-12a), 69.6 (C-5), 47.8 (C-5a), 44.3 (C-4a), 39.1 (C-6), 32.2 (C-4), 16.3 ($CH_3$). The signals of C—X, C—Z lay under the peal of the NMR solvent.

The coupling reaction between D9 and dopamine hydrochloride, in the presence of EDCl/HOBt as coupling reagent, was unsuccessful. The following procedure was employed for the coupling reaction: D9 (1 eq) was dissolved in dry DMF (2 mL) and EDCl (1 eq.) and HOBt (1 eq.) were added to the stirred solution at 0° C. during 30 min. The solution was stirred for additional 1.5 h at room temperature. Then, TEA (3 eq.) and dopamine hydrochloride were added to the reaction mixture. The solution was monitored by reverse phase TLC but no changes were observed, even when the solution was kept overnight under stirring at room temperature.

Synthesis of D10 by Coupling of Dopamine with Succinic Anhydride

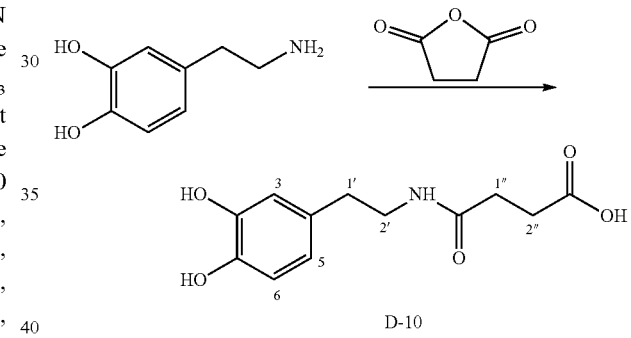

In a dark round bottom flask equipped with a septum, dopamine hydrochloride (0.2 g, 1.0 mmol) was dissolved in pyridine (3 mL) and succinic anhydride was slowly added (140 mg, 1.4 mmol). The mixture was stirred for 24 h, when TLC (EtOAc:MeOH 9:1) showed the complete conversion of dopamine (Rf 0) into a faster moving product (Rf 0.27). The solvent was evaporated under reduced pressure and the residue was treated with MeOH to afford D10 (1.22 g, 91%), as a white, amorphous solid; 1H NMR ($(CD_3)_2CO$, 500 MHz) δ: 6.72 (d, 1H, $J_{5,6}$=8.0 Hz, H-6), 6.71 (d, 1H, $J_{3,5}$=2.0 Hz, H-3), 6.53 (dd, 1H, $J_{3,5}$=2.0, $J_{5,6}$=8.0 Hz, H-5), 3.35 (t, 2H, $J_{1',2'}$=6.7 Hz, H-2'), 2.64 (t, 2H, $J_{1',2'}$=6.7 Hz, H-1'), 2.59 (t, 1H, $J_{1'',2''}$=7.0 Hz, H-1''), 2.47 (t, 1H, $J_{1'',2''}$=7.0 Hz, H-2''); $^{13}$C NMR ($CDCl_3$, 125.7 MHz) δ: 174.1, 172.6 (CO), 145.5, 144.1 (C-1,2), 131.7 (C-4), 120.6 (C-5), 116.4, 115.8 (C-3, 6), 41.8 (C-2'), 35.6 (C-1'), 31.0×2 (C-1'',2'').

The attempted coupling of the dopamine derivative (D10) with D5 using DCC or EDCl as coupling agents was unsuccessful. The general procedure for the coupling reaction was the following:

Equimolar quantities (0.07 mmol) of D10 and D5 in dry DMF (1 mL) were stirred under argon atmosphere for 30 min. Then, the coupling agent (2 eq) was added to the mixture at room temperature. The reaction was stirred for 12 h and no formation of the expected product was observed by

Synthesis of N-tert-butyloxycarbonyl-2-(3,4-dihydroxyphenyl)ethanamine (N-Boc Dopamine, 11)

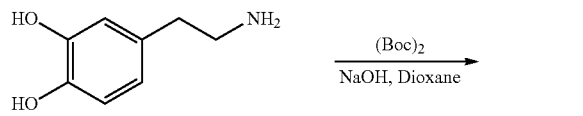

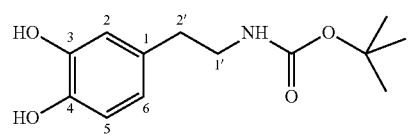

In a dark round bottom flask, dopamine hydrochloride (1.0 g, 5.3 mmol) was dissolved in a previously sonicated mixture of dioxane (10 mL) and 1M aqueous NaOH (5 mL). The mixture was stirred for 10 min and di-tert-butyl dicarbonate (1.3 g, 5.8 mmol) was added. The reaction was stirred at room temperature for 4 h, under $N_2$ atmosphere, when TLC (hexane:EtOAc 2:8 with 1 drop of AcOH) showed the complete conversion of dopamine (Rf 0) into a fast moving product (Rf 0.8). The solution was acidified with HCl (1M) to pH 2, and then was extracted with EtOAc (×3). The organic layer was dried ($Na_2SO_4$) and concentrated to afford 11 (1.22 g, 91%); $^1$H NMR (($CD_3$)$_2$CO, 500 MHz) δ: 7.69 (brs, 2H, OH), 6.73 (d, 1H, $J_{5,6}$=8.0 Hz, H-5), 6.70 (d, 1H, $J_{2,6}$=2.0 Hz, H-2), 6.53 (dd, 1H, $J_{2,6}$=2.0, $J_{5,6}$=8.0 Hz, H-6), 5.87 (brs, 1H, NH), 3.20 (dt, 2H, J=6.1 Hz, H-1'), 2.62 (t, 2H, J=6.1 Hz, H-2'), 1.39 (s, 9H, ($CH_3$)$_3$CON); $^{13}$C NMR (CDCl$_3$, 125.7 MHz) δ:156.6 (CO), 145.8, 144.2 (C-3,4), 132.1 (C-1), 120.8 (C-6), 116.6. 116.0 (C-2,5), 78.4 (($CH_3$)$_3$CON), 43.1 (C-1'), 36.3 (C-2'), 28.6 (($CH_3$)$_3$CON); HRMS (ESI) m/z [M+Na]$^+$ calcd for $C_{13}H_{19}NNaO_4$ 276.1206; found 276.1204.

The signal of the methylene vicinal to N (H-1') is seen as two partially overlapped triplets because of the two rotamers in rapid interconversion due to the tert-butyl carbamate.

Synthesis of N-tert-butyloxycarbonyl-2-(3,4-bis(benzyloxy)phenyl)ethanamine (Di-O-benzyl-N-Boc Dopamine, 12)

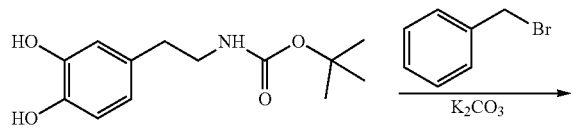

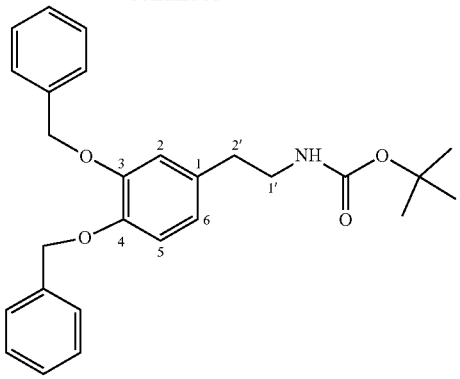

A suspension of 11 (1.3 g, 5.3 mmol) dissolved in DMF (20 mL) and $K_2CO_3$ (4.4 g, 32 mmol) was stirred at room temperature for 30 min. Upon cooling to 0° C. (ice bath), benzyl bromide (1.8 mL, 16 mmol) was added dropwise with continuous stirring. The reaction was kept for 24 h, when monitoring by TLC (hexane: EtOAC 7:3) showed the conversion of the starting compound (Rf=0.35) into a less polar spot (Rf=0.57). Water was added and cooled to 0° C. leading to the formation of a solid product. The mixture was kept in ice bath with stirring for 1 h, to complete the precipitation. The solid was filtered, washed with water and dried to give 12 (1.65 g, 72%); $^1$H NMR (CDCl$_3$, 300 MHz) δ: 7.48-7.27 (m, 10H, H-aromatic), 6.87 (d, 1H, $J_{5,6}$=8.1 Hz, H-5), 6.80 (d, 1H, $J_{2,6}$=2.0 Hz, H-2), 6.70 (dd, 1H, $J_{5,6}$=8.1, $J_{2,6}$=2.0 Hz, H-6), 5.14, 5.13 (2 s, 2H each, OCH$_2$Ph), 4.49 (brs, 1H, NH), 3.31 (dt, 2H, $J_{1',2'}$=6.7 Hz, H-1'), 2.69 (t, 2H, $J_{1',2'}$=6.7 Hz, H-2'), 1.44 (s, 9H, ($CH_3$)$_3$C); $^{13}$C NMR (CDCl$_3$, 75 MHz) δ: 155.9 (NHCO), 149.0, 147.7 (C-3,4), 137.5, 137.3, 132.4, 128.5, 127.8, 127.4, 127.3, 121.7, 115.9, 115.5 (C-1,2,5,6), 71.5, 71.4 (OCH$_2$Ph), 41.8 (C-1'), 35.7 (C-2'), 28.4 (($CH_3$)$_3$C), 27.7 (($CH_3$)$_3$C). HRMS (ESI) m/z [M+Na]$^+$ calcd for $C_{27}H_{31}NNaO_4$ 456.2153; found 456.2145.

As for 11, the signal of the methylene vicinal to N (H-1') is seen as two partially overlapped triplets because of the two rotamers in rapid interconversion due to the tert-butyl carbamate.

Synthesis of 2-(3,4-bis(benzyloxy)phenyl)ethanamine (13)

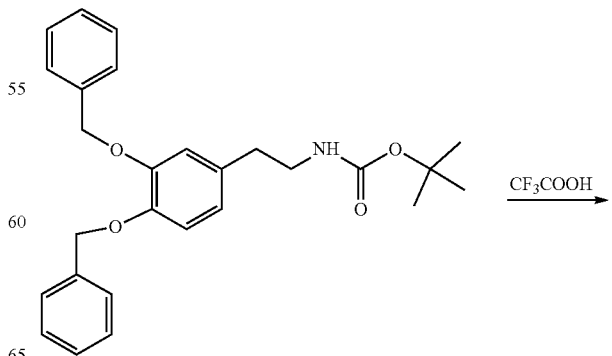

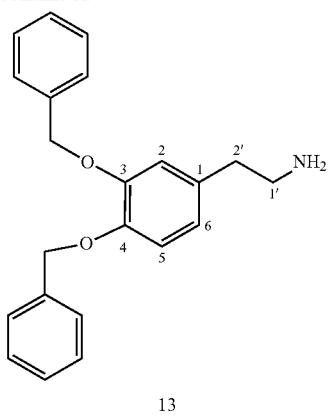

13

To a solution of 12 (0.84 g, 1.94 mmmol) in CH$_2$Cl$_2$ (11 mL) was added trifluoroacetic acid (1.7 mL) and stirred at room temperature for 2 h. The reaction was monitored by TLC (hexane:EtOAc 3:7), revealing the conversion of the starting material (Rf 0.57) into a polar product (Rf 0). The pH of the solution was adjusted to 9 by addition of 1M NaOH, and rapidly extracted with CH$_2$Cl$_2$ (20 mL). The organic layer was washed with saturated aqueous NaCl, dried and concentrated to afford 13 (0.46 g, 72%); $^1$H NMR (CDCl$_3$, 300 MHz) δ: 7.52-7.25 (m, 10H, H-aromatic), 6.90 (d, 1H, J$_{5,6}$=8.1 Hz, H-5), 6.81 (d, 1H, J$_{2,6}$=1.9 Hz, H-2), 6.71 (dd, 1H, J$_{5,6}$=8.1, J$_{2,6}$=1.9 Hz, H-6), 5.17, 5.15 (2 s, 2H each, OCH$_2$Ph), 2.87 (t, 2H, J$_{1',2'}$=6.7 Hz, H-1'), 2.64 (t, 2H, J$_{1',2'}$=6.7 Hz, H-2'), 1.81 (brs, 2H, NH$_2$); $^{13}$C NMR (CDCl$_3$, 75 MHz) δ: 149.0, 147.6 (C-3,4), 137.5, 137.4, 128.5, 127.8, 127.4 (C-aromatic Ph), 133.2 (C-1), 121.8 (C-6), 116.1 (C-2), 115.4 (C-5), 71.5, 71.4 (OCH$_2$Ph), 43.4 (C-1'), 39.3 (C-1'); HRMS (ESI) m/z [M]$^+$ calcd for C$_{22}$H$_{24}$NO$_2$ 334.1802. found 334.1804.

Synthesis of 14 by Addition of 13 to Succinic Anhydride, and Attempted Coupling of 14 with D5

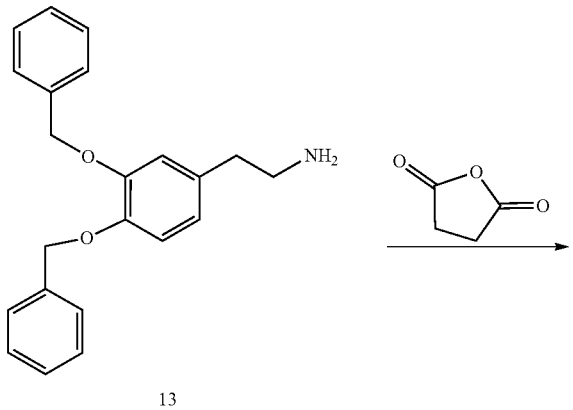

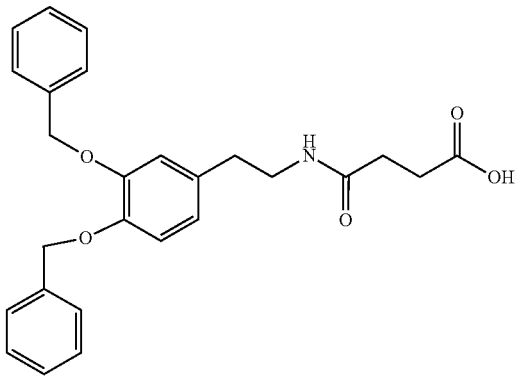

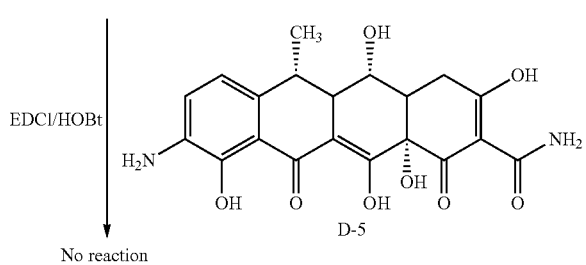

No reaction

To a solution of 13 (115 mg, 0.3 mmol) in DMF (3 mL) was added K$_2$CO$_3$ (140 mg, 1.0 mmol) and the solution was stirred for 10 min. Upon addition of succinic anhydride (40 mg, 0.4 mmol), the solution was stirred at room temperature for 4 h. Examination by TLC (EtOAc with 2 drops of HAcO) showed complete formation of a faster moving compound (Rf 0.25). The reaction mixture was acidified with 1M HCl (≈0.5 mL) to pH 2 and water was added to induce precipitation. The mixture was stirred for 1 h in an ice bath and the solid formed was filtered. The solid was purified by column chromatography (hexane: EtOAc 5:5-+3:7, with 1% HAcO) to afford 14 (127 mg, 84%); $^1$H NMR (CDCl$_3$, 200 MHz) δ: 7.49-7.22 (m, 10H, H-aromatic), 6.88 (d, 1H, J$_{5,6}$=8.1 Hz, H-5), 6.76 (brd, 1H, J$_{2,6}$=2.1 Hz, H-2), 6.66 (dd, 1H, J$_{5,6}$=8.1, J$_{2,6}$=2.1 Hz, H-6), 5.76 (t, J$_{NH,c}$=5.9 Hz, NH), 5.15.

5.14 (2 s, 2H each, OCH$_2$Ph), 3.44 (q, 2H, J$_{1',2'}$=J$_{1',NH}$=6.5 Hz, H-1'), 2.66 (m, 4H, H-2',b), 2.36 (t, 2H, J$_{a,b}$=6.4 Hz, H-a);

$^1$H NMR ((CD$_3$)$_2$SO, 500 MHz) δ: 7.49-7.29 (m, 10H, H-aromatic), 7.90 (brs, 1H, —NH), 6.96 (d, 1H, J$_{5,6}$=8.2 Hz, H-5), 6.94 (d, 1H, J$_{2,6}$=1.9 Hz, H-2), 6.71 (dd, 1H, J$_{5,6}$=8.2, J$_{2,6}$=1.9 Hz, H-6), 5.11, 5.08 (2 s, 2H each, OCH$_2$Ph), 3.20 (dd, 2H, J$_{1',2'}$=7.5, J$_{1',NH}$=5.6 Hz, H-1'), 2.60 (d, 2H, J$_{c,d}$=7.5 Hz, H-2'), 2.41 (d, 2H, J$_{a,b}$=6.7 Hz, H-a), 2.29 (d, 2H, J$_{a,b}$=6.7 Hz, H-b); $^{13}$C NMR ((CD$_3$)$_2$SO, 125.7 MHz) δ: 173.9 (COOH), 170.9 (CONH), 148.2, 146.7 (C-3,4), 132.7 (C-1), 128.4 127.7×2, 127.6, 127.5, (OCH$_2$Ph) 121.1 (C-6), 115.1 (C-2), 114.7 (C-5), 70.2, 70.1 (OCH$_2$Ph), 40.4 (C-1'), 34.7 (C-2'), 30.1 (C-b), 29.2 (C-a)

HRMS (ESI) m/z [M]$^+$ calcd for C$_{26}$H$_{28}$NO$_5$ 434.1962, found 434.1952.

The attempted coupling reaction between 14 and D5 in the presence of EDCl/HOBt, as well as with other coupling reagents, was unsuccessful Synthesis of the conjugate doxycycline-dopamine [N$^1$-(4-dedimethylamino doxycycline-9-yl)-N$^4$-(3,4-dihydroxyphenethyl)succinamide, D16]

A solution of 14 (156 mg, 0.36 mmol) in anhydrous DMF (2 mL) was cooled to −5° C. and ethyl chloroformate (33 μL, 0.36 mmol) and triethylamine (50 μL, 0.36 mmol) were added dropwise during 15 min. The intermediate anhydride-carbonate 15 was not isolated and, after additional 15 min, D5 (100 mg, 0.24 mmol) in dry DMF (2 mL) and fine powdered NaHCO$_3$ (20 mg, 0.24 mmol) were successively added. The reaction was stirred for 2 h, when silicagel TLC (EtOAc: C$_5$H$_5$N: H$_2$O 9:2.5:1) showed the formation of a slightly higher moving spot (Rf 0.70) compared to D5 (Rf 0.68). In contrast to D5, which revealed under UV irradiation only at 254 nm, the product revealed at A 254 and 365 nm. The reaction was also monitored using reverse phase TLC (H$_2$O:MeCN 1:1) confirming the formation of a new spot (Rf 0.35) less moving than D5 (Rf 0.75). The crude mixture was filtered to remove the excess of NaHCO$_3$ and acidified to pH 2 with HCl (c). The solvent was removed by evaporation under reduced pressure and the oily residue was washed with 5% aqueous solution LiCl to remove the excess of DMF.

Purification by reverse phase column chromatography (MeOH:H$_2$O 1:1→3:2) followed by evaporation of the solvent, afforded D16, as yellowish powder (200 mg, 60%). [α]$_D^{20}$ −30.1 (c 0.2, MeOH); $^1$H NMR (CD$_3$OD, 500 MHz); δ: 8.16 (d, 1H, J$_{7,8}$=8.3 Hz, H-8), 7.47-7.22 (m, 10H, Aromatics), 6.90 (d, 1H, J$_{f,j}$=1.0 Hz, H-f), 6.88 (d, 1H,

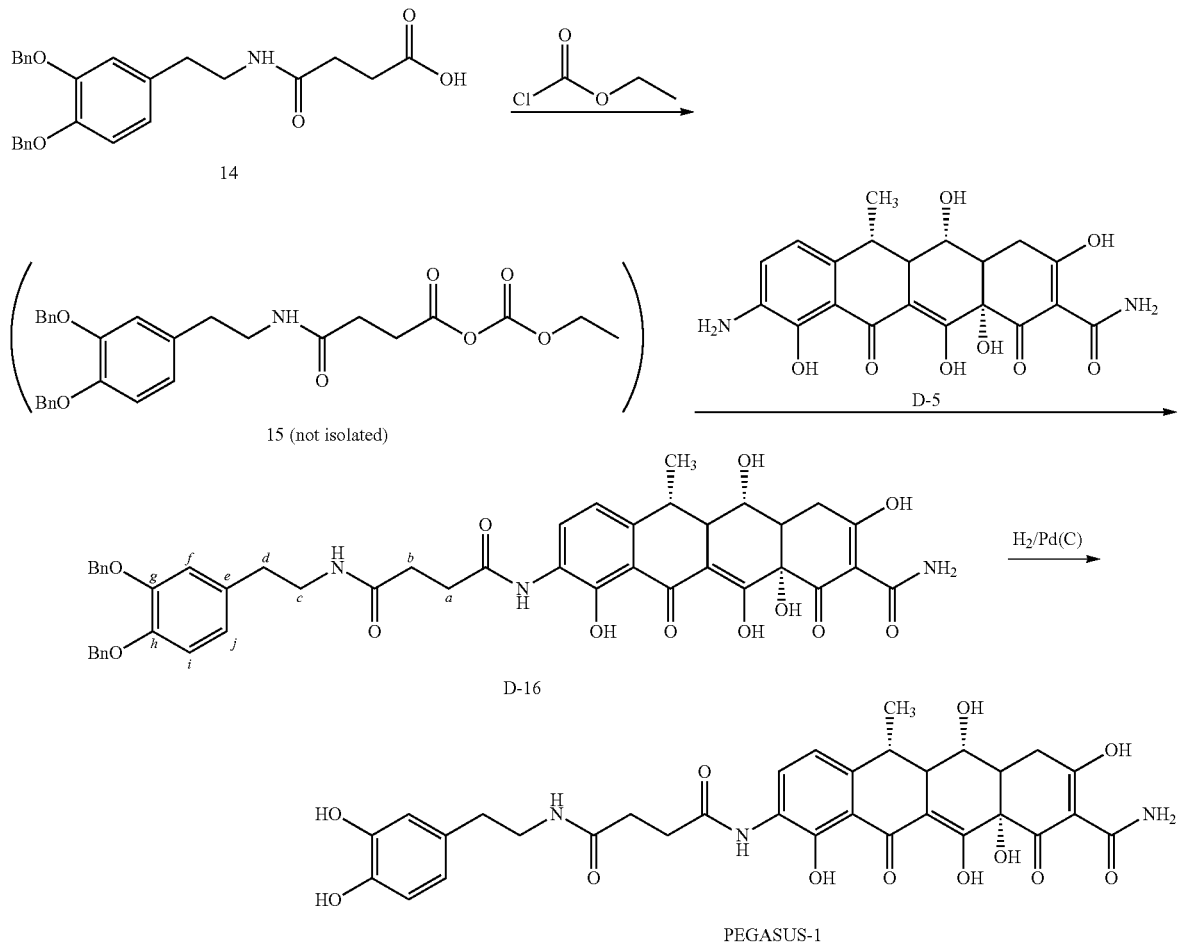

J$_{i,j}$=8.2 Hz, H-i), 6.80 (d, 1H, J$_{7,8}$=8.3 Hz, H-7), 6.72 (d, 1H, J$_{f,i}$=7.9, J$_{i,j}$=1.0 Hz, H-J), 5.12-5.00 (m, 6H, CH$_2$Ar), 3.60 (q, 1H, J$_{4a,5}$=10.7, J$_{5a,5}$=8.0 Hz, H-5), 3.35 (t, 2H, J=7.2 Hz,

CH$_2$-c), 3.03 (brd, 1H, J$_{4,4'}$=18.0 Hz, H-4), 2.90 (brd, 1H, J$_{4,4'}$=18.0 Hz, H-4'), 2.69 (t, 2H, J=7.3 Hz, CH$_2$-d), 2.56 (m, 1H, J=6.7 Hz, H-6), 2.51, 2.42 (2 t, 4H, J=6.8 Hz, CH$_2$-a, CH$_2$-b), 2.35-2.28 (m, 2H, H-4a,5a), 1.43 (d, 3H, J$_{6,Me}$=6.7 Hz, CH$_3$); $^{13}$C NMR (CD$_3$OD, 125.7 MHz) δ: 196.4, 195.4, 194.6 (C-1,3,11), 175.0, 174.6, 174.2, 173.2 (CONH$_2$, 2 CONH, C-12), 153.5 (C-10), 150.3, 148.7 (C-g, C-h), 144.2 (C-6a), 134.3 (C-e), 138.8-128.8 (C-aromatic of Ph groups and C-8), 126.7 (C-9), 122.9 (C-J), 117.1, 117.0 (C-f, C-1), 116.6 (C-10a), 116.1 (C-7), 108.0 (C-11a), 100.1 (C-2), 72.6, 72.4 (C-12a, CH$_2$Ar), 69.9 (C-5), 48.0, 44.9 (C-4a,5a), 42.0 (C-c), 39.6 (C-6), 36.0 (C-d), 32.0, 31.4 (C-a, C-b), 30.2 (C-4), 16.2 (CH$_3$); HRMS (ESI) m/z [M+Na]$^+$ calcd for C$_{46}$H$_{46}$N$_3$O$_{12}$ 832.3076, found 832.3078.

Hydrogenolysis of D16: Synthesis of Pegasus

A solution of compound D16 in MeOH (5 mL) containing 10% Pd/C (50 mg) was subjected to hydrogenation at 44 psi (3 atm) for 20 h. The mixture was diluted with methanol (10 mL) and the catalyst was filtered through a celite pad and washed with methanol (4 mL). The filtrate and washings were collected and concentrated. The residue was dissolved in the minimum amount of methanol and precipitation was induced upon addition of water. The resulting brownish-yellow solid was isolated by centrifugation and dried to afford Pegasus (85 mg, 54%); [α]$_D^{20}$ −16.7 (c 1.1, MeOH); $^1$H NMR (CD$_3$OD, 500 MHz); δ: 8.16 (d, 1H, J$_{7,8}$=7.9 Hz, H-8), 6.87 (d, 1H, J$_{7,8}$=7.9 Hz, H-7), 6.67 (d, 1H, J$_{i,j}$=7.9 Hz, H-i), 6.64 (s, 1H, H-f), 6.52 (d, 1H, J$_{j,i}$=7.9 Hz, H-J), 3.63 (q, 1H, J$_{4a,5}$=10.2, J$_{5a,5}$=8.3 Hz, H-5), 3.35 (m, 2H, overlapped with MeOD, CH$_2$-c), 3.15 (brd, 1H, J$_{4,4'}$=17.7 Hz, H-4), 2.92 (dd, 1H, J$_{4,4'}$=17.7 Hz, H-4'), 2.74, 2.55 (brt, 2H, CH$_2$-a, CH$_2$-b), 2.63 (t, 2H, J=6.5 Hz, CH$_2$-d), 2.63 (1H, overlapped under CH$_2$-d, H-6), 2.34 (m, 2H, H-4a,5a), 1.50 (d, 3H, J$_{6,Me}$=6.4 Hz, CH$_3$); $^{13}$C NMR (CD$_3$OD, 125.7 MHz) δ:196.4-195.5 (C-1,3,11), 175.1, 175.0, 174.5, 173.3 (CONH$_2$, 2 CONH, C-12), 153.6 (C-10), 146.2, 144.7 (C-g, C-h), 144.4 (C-6a), 132.1 (C-e), 129.3 (C-8), 126.6 (C-g), 121.1 (C-f), 116.8, 116.3 (C-f, C-J), 116.7 (C-10a), 116.1 (C-7), 108.0 (C-11a), 100.0 (C-2), 76.1 (C-12a), 69.9 (C-5), 48.1, 44.9 (C-4a,5a), 42.4 (C-c), 39.7, 35.9 (C-6, C-d), 33.1, 32.3 (C-a, C-b), 31.3 (C-4), 16.2 (CH$_3$); HRMS (ESI) m/z [M+Na]$^+$ calcd for C$_{32}$H$_{33}$N$_3$NaO$_{12}$ 674.1956, found 674.1972.

Example 3—Characterization of the Capacity of the Compound of the Invention to Interfere with Toxic AS Aggregation In order to evaluate the effect of Pegasus (D9) on AS amyloid fibril formation, aggregation reactions were performed according to LeVine (LeVine H, 3rd. Thioflavine T interaction with synthetic Alzheimer's disease beta-amyloid peptides: detection of amyloid aggregation in solution. *Protein Sci* 1993; 2(3): 404-10; LeVine H, 3rd. Quantification of beta-sheet amyloid fibril structures with thioflavin T. *Methods Enzymol* 1999; 309: 274-84.). In brief, the formation of cross-β structures were followed by adding Thioflavin T (ThT), a fluorescent cross-β reporter probe, to aliquots extracted from the incubation mixture at different times.

Expression and purification of recombinant human AS were performed as previously described (Hoyer W, Antony T, Cherny D, Heim G, Jovin T M, Subramaniam V. Dependence of AS aggregate morphology on solution conditions. *J Mol Biol* 2002; 322(2): 383-93), and purity was assessed by SDS-PAGE. Monomeric AS stock solutions were prepared in 20 mM HEPES, pH 7.4. Prior to measurements, protein solutions were filtered and centrifuged for 30 min at 12,000×g. The protein concentration was determined by absorbance at 275 nm using the extinction coefficient ε275=5600 cm$^{-1}$ M$^{-1}$. The aggregation protocol used was adapted from previous studies (Kaylor J, Bodner N, Edridge S, Yamin G, Hong D P, Fink A L. Characterization of oligomeric intermediates in alpha-synuclein fibrillation: FRET studies of Y125W/Y133F/Y136F alpha-synuclein. *J Mol Bio*/2005; 353(2): 357-72; Danzer K M, Haasen D, Karow A R, et al. Different species of alpha-synuclein oligomers induce calcium influx and seeding. *J Neurosci* 2007; 27(34): 9220-32; Avila C L, Torres-Bugeau C M, Barbosa L R, et al. Structural characterization of heparin-induced glyceraldehyde-3-phosphate dehydrogenase protofibrils preventing alpha-synuclein oligomeric species toxicity. *J Biol Chem* 2014; 289(20): 13838-50; Gonzalez-Lizarraga F, Socias S B, Avila C L, et al. Repurposing doxycycline for synucleinopathies: remodelling of alpha-synuclein oligomers towards non-toxic parallel beta-sheet structured species. *Scientific reports* 2017; 7: 41755).

Figure 2:
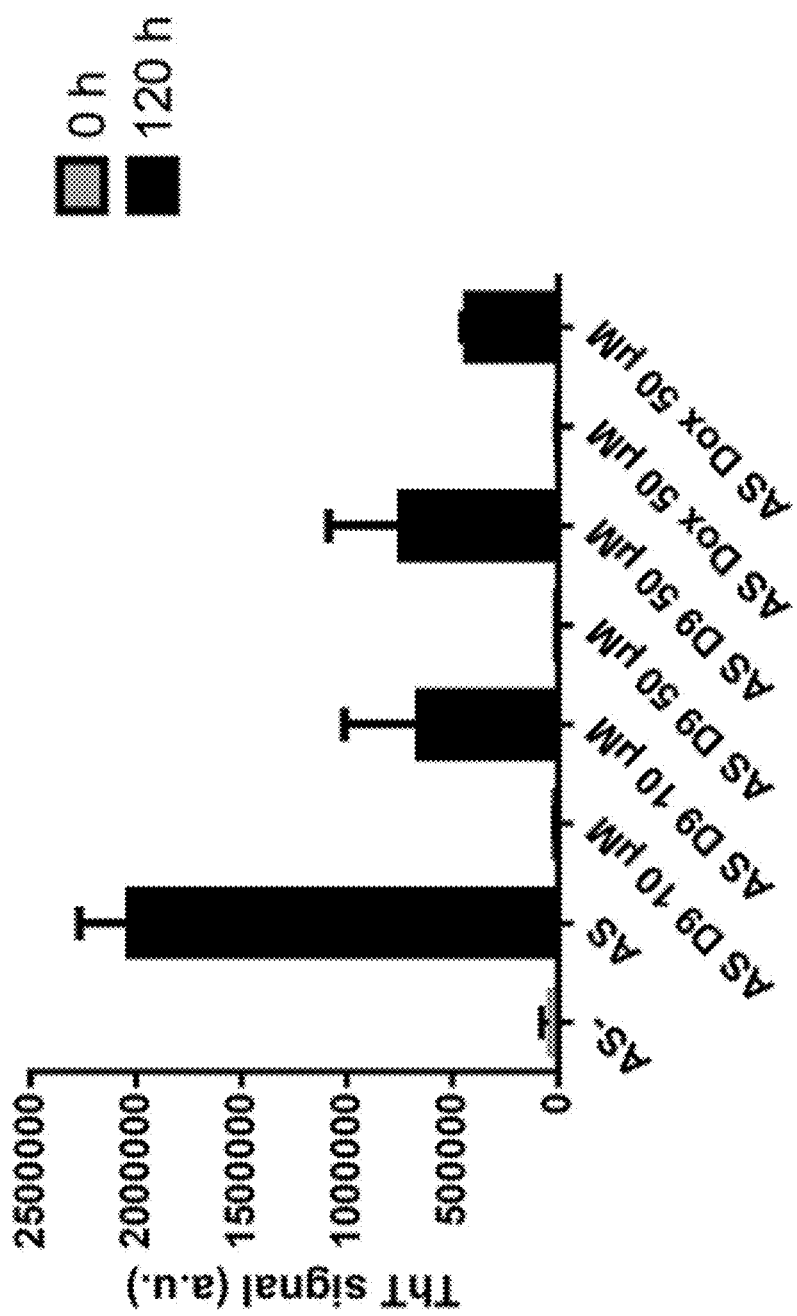
FIG. 2. Effects of Pegasus (D9) on AS amyloid aggregation. Fluorescence emission intensity of 25 µM thioflavin T in a solution containing 70 µM AS alone or with the addition of D9 10 µM and 50 µM, incubated 0 h and 120 h at 37° C. 600 rpm. A solution containing 70 µM AS and doxycycline 50 µM (DOX) was included as an internal control.

For aggregation reactions, aliquots of monomeric AS (70 μM) in 20 mM HEPES, pH 7.4 were incubated in a Thermomixer comfort (Eppendorf) at 37° C. and 600 rpm in the absence or presence of 10 or 50 μM D9. Aggregation was monitored with a Horiba FluoroMax-4 spectrofluorometer using the ThT fluorescence assay. As observed in FIG. 2, D9 was able to inhibit AS aggregation (both at 10 and 50 μM), just as potently as the positive control doxycycline (FIG. 2).

Example 4—Determination of Antibiotic Activity of the Compound of the Invention

In order to examine the antibiotic activity of the compounds synthesized in Example 1, an assay was performed using *E. coli* DH5α (Gram(−)), as a sensitive, indicator strain.

The inventors used the serial doubling dilutions technique for determining the minimum inhibitory concentration (MIC) in solid LB medium, with a starting concentration of 2 mg/ml and a volume of 10 μl in each dilution.

The antibacterial activities of test compounds were evaluated using the disc diffusion method (Kavanagh, F. *Dilution methods of antibiotic assays in Analytical Microbiology.* 1963; Pomares M F, Vincent P A, Farias R N, Salomón RA. *Protective action of ppGpp in microcin J25-sensitive strains.* J Bacteriol. 2008-190:4328-34). Briefly, filter-paper discs impregnated with 10 μl of two-fold serial dilutions of the test compounds, and were placed onto LB solid medium Petri dishes. Then, aliquots (50 μl) of an *E. coli* DH5a culture in stationary phase were mixed with 3 ml of top agar (0.7% agar) and overlaid onto the plates. After overnight incubation at 37° C., the plates were examined for different degrees of inhibition. Inhibition degrees produced by the test compound are expressed as Minimum Inhibitory Concentrations (MICs), defined as the lowest concentration of a compound that inhibit visible growth of bacteria. Each test was performed in duplicate vs. the reference compound Doxycycline. As observed in Table 1, the reference compound doxycycline presented a MIC of 31.25 μg/ml, while D9, the compound of the invention, presented no antibiotic activity at the concentrations tested.

TABLE 1

Determination of the antibiotic activities of Pegasus (D9) and other related compounds by disc diffusion assay

| COMPOUND | MIC | RATE MIC Compound/Doxycycline |
|---|---|---|
| Doxycycline | 31.25 µg/ml | — |
| D1 | 31.25 µg/ml | 1 |
| D3 | 500 µg/ml | 16 |
| D4 | 1000 µg/ml | 32 |
| D5 | 250 µg/ml | 8 |
| D6 | 2000 µg/ml | 64 |
| D7 | — | — |
| D9 (Pegasus) | — | — |
| D3D | 1000 µg/ml | 32 |
| Acop4 | — | — |

Example 5—Cytotoxicity of the Compound of the Invention 5.1. Effect of Pegasus Cytotoxicity on Neuroblastoma SH-SY5Y Cells The impact of Pegasus (D9) on cellular viability was studied in SH-SY5Y neuroblastoma cell lines using the colorimetric Thiazolyl Blue Tetrazolium Blue (MTT) metabolic activity assay (Mosmann T. Rapid colorimetric assay for cellular growth and survival: application to proliferation and cytotoxicity assays. *J Immunol Methods* 1983; 65(1-2): 55-63), which reports viable cell number based on mitochondrial activity.

SH-SY5Y cells were seeded in 96-well plates at 15,000 cells/well with 100 µl of DMEM supplemented with 10% Fetal Bovine Serum (FBS) and 1% Antibiotics/Antimycotics, and incubated for 24 h at 37° C. and 5% $CO_2$. Afterwards, cells were treated with a 25 µl aliquot of a D9 solution 5 µM, 50 µM or 100 µM (final concentration in well 1 µM, 10 µM and 20 µM, respectively) and incubated for 24 h. To determine cell viability, the MTT assay was used as previously described by Mosmann (1983). All experiments were performed in sextuplicate, and the relative cell viability (%) was expressed as a percentage relative to the untreated control condition.

Figure 3:
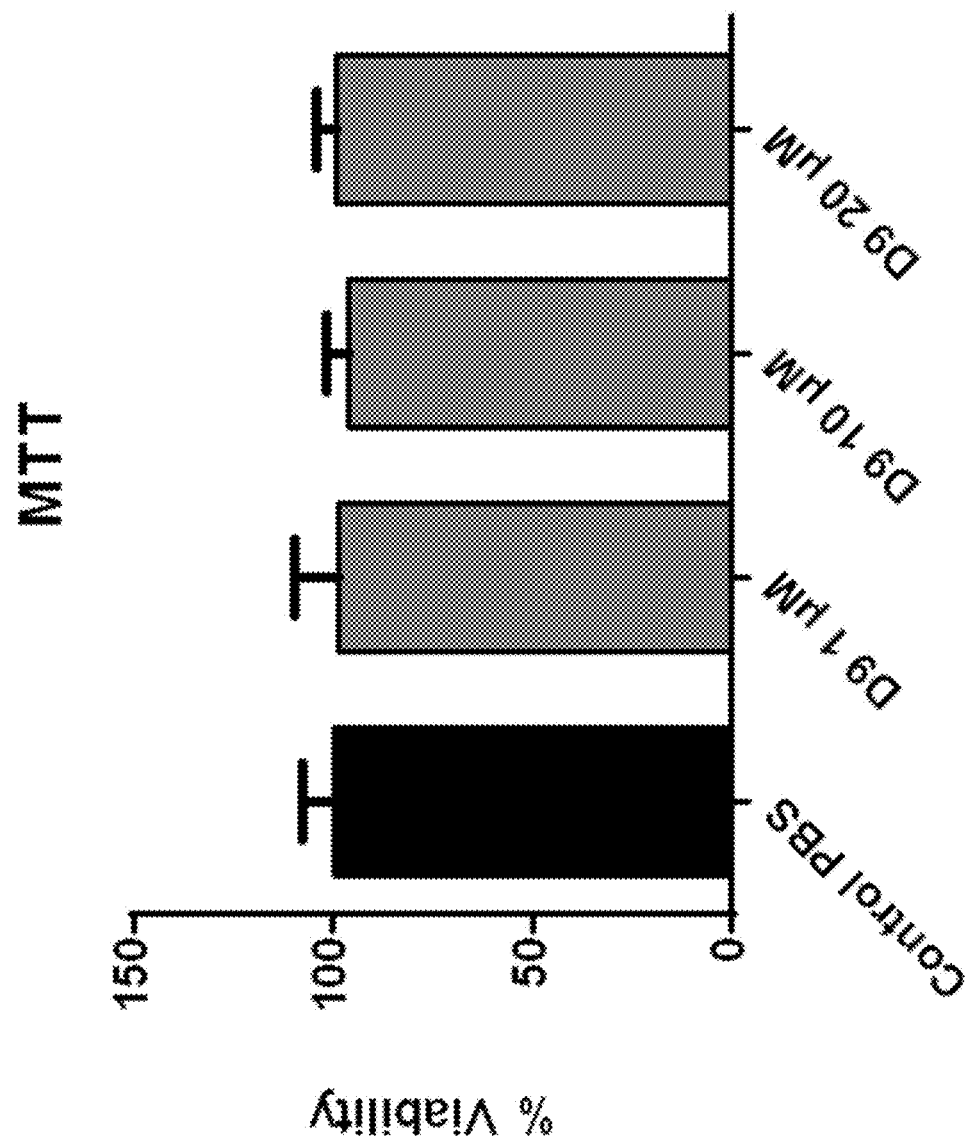
FIG. 3. MTT assay showing the effect of Pegasus (D9) on cytotoxicity in neuroblastoma SH-SY5Y cells.

No significant differences were observed in MTT turnover between cells treated with up to 20 µM of Pegasus and controls, indicating that Pegasus (at 1, 10 and 20 µM) had no cytotoxic effect on SH-SY5Y cells (FIG. 3).

5.2. Effect of Pegasus Cytotoxicity on Microbial Bv2 Cell Line

The ability of D9 to induce cytotoxicity was also studied using the MTT assay on Bv2 cells, a microglial cell line derived from the C57/BL6 murine model. For this, Bv2 cells were incubated in the presence and in the absence of different Pegasus concentrations at 37° C. Bv2 cells retain the morphology and functional characteristics of microglia and are therefore a widespread microglial model. These cells are immortalized by v-raf/v-myc carrying J2 retrovirus, and express nuclear v-myc and the cytoplasmic v-raf oncogene products as well as the env gp70 antigen at the surface level.

Figure 4:
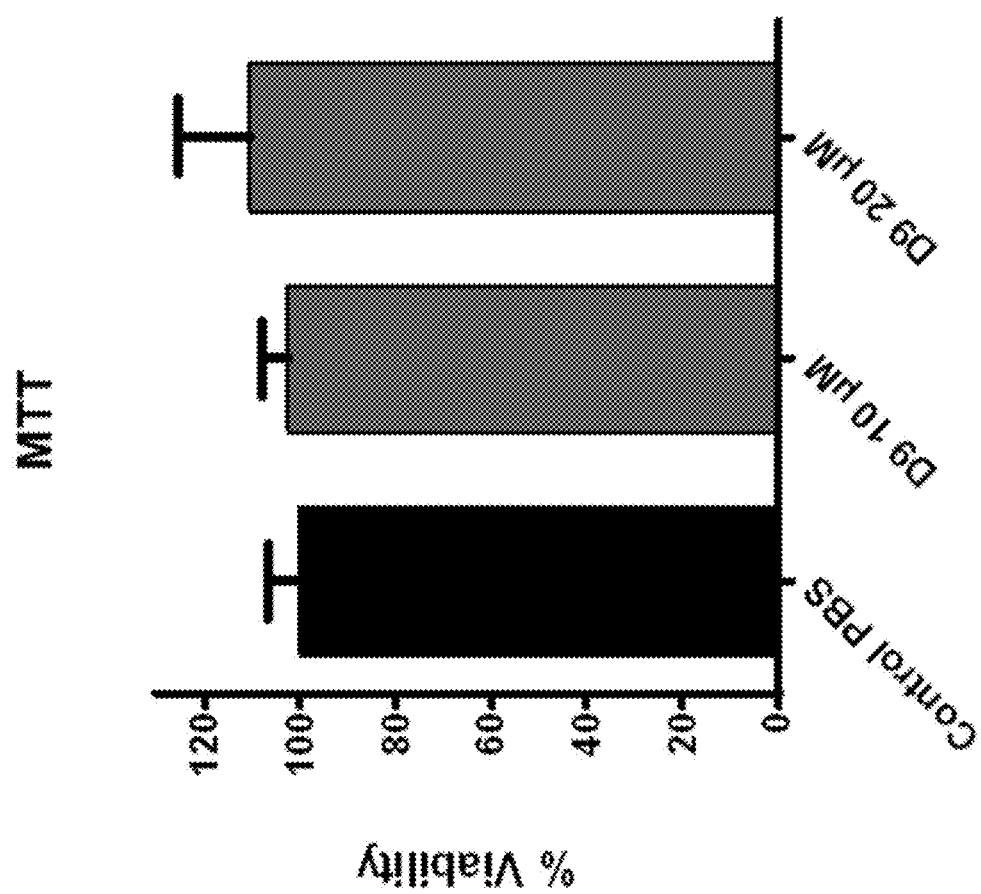
FIG. 4. MTT assay showing the effect of Pegasus (D9) on cytotoxicity in microglial Bv2 cell line.

Bv2 cells were seeded in Poly-L-Lysine-treated 96-well plates at 15,000 cells/well and in 100 µl of DMEM supplemented with 10% Fetal Bovine Serum (FBS) and 1% Antibiotics/Antimycotics (PSA) and incubated for 24 h at 37° C. and 5% $CO_2$. Afterwards, cells were treated with a 25 µl aliquot of a 50 µM and 100 µM Pegasus solution (final concentration in well 10 µM and 20 µM) and incubated for 24 h. To determine cell viability, the colorimetric MTT metabolic activity assay was used as previously described by Mosmann. All experiments were performed in sextuplicate, and the relative cell viability (%) was expressed as a percentage relative to the untreated control condition. Results showed that Pegasus, at concentrations up to 20 µM, did not induce cell toxicity since no significant change in MTT signal was obtained (FIG. 4).

Example 6—Pegasus Reduces the Levels of Intracellular Reactive Oxygen Species Induced by $AS_f$ in SH-SY5Y Cells Among the pathophysiological mechanisms indicated as major pathways of neurodegeneration, mitochondrial dysfunction and oxidative stress have been proven to enhance neuroinflammation and protein misfolding. Furthermore, these processes also trigger mitochondrial dysfunction and oxidative stress, propelling a vicious circle with fatal consequences for cells, especially neurons. Accordingly, AS aggregates are capable of inducing increased production of reactive oxygen species (ROS) and thereby, exacerbating the neurodegenerative process.

In order to characterize the antioxidant properties of D9, its protective action on the AS-induced production of reactive oxygen species (ROS) in a cellular model was assessed. For this, SH-SY5Y cells were treated with fibrils of AS ($AS_1$) (AS incubated 120 h at 37° C. and 600 rpm), and the reactive oxygen species produced were examined using the CellROX® Orange Reagent (Invitrogen), which undergoes oxidation by ROS to form a stable fluorescent compound.

Figure 5:
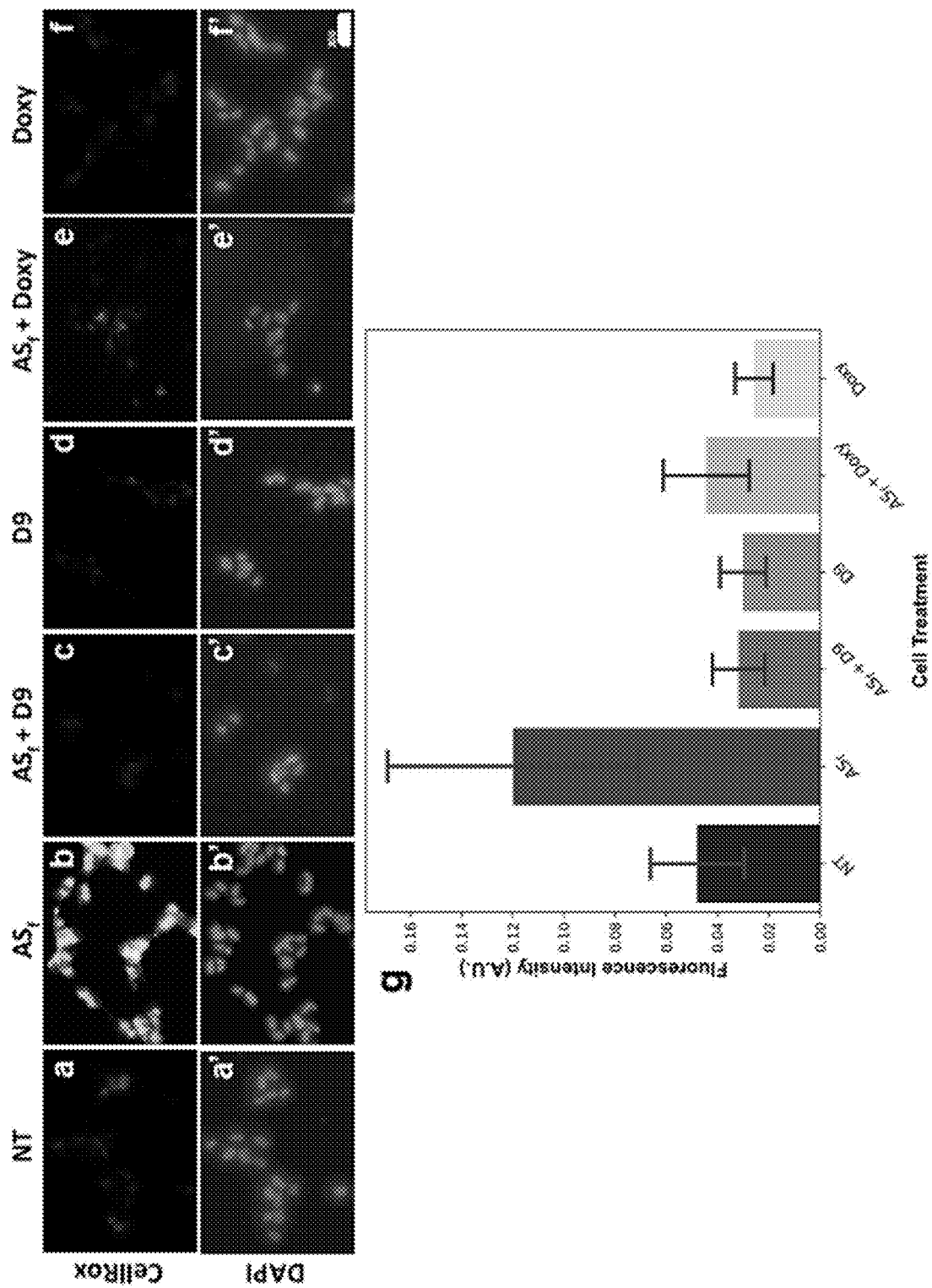
FIG. 5. CellRox assay for determining the effect of Pegasus (D9) on intracellular reactive oxygen species induced by α-synuclein fibrils ($AS_f$) in SH-SY5Y cells.

As shown in FIG. 5, SH-SY5Y cells were either left untreated (non-treated, NT), or treated with 7 µM $AS_f$ ($AS_f$), 7 µM of $AS_f$+D9 10 µM ($AS_f$+D9), and D9 10 µM alone as a control (D9). In addition, cells were also treated with doxycycline 10 µM+7 µM $AS_f$ ($AS_f$+Doxy) as a positive control, and 10 µM doxycycline alone (Doxy). All conditions were incubated 24 h at 37° C. and 5% $CO_2$. After treatment and incubation, intracellular reactive oxygen species were revealed with 5 µM CellROX® Orange Reagent (Invitrogen) by adding the probe for 30 min, washing 3 times with PBS, and a subsequent analysis by fluorescence microscopy. Fluorescent images of randomly chosen fields were acquired with identical acquisition parameters using a Zeiss Axio Vert.A1 inverted fluorescence microscope.

As expected, SH-SY5Y cells displayed an increased amount of intracellular ROS when treated with $AS_f$, as indicated by a stronger emission of the fluorescence probe CellROX® Orange Reagent (FIG. 5*a,b*). Conversely, when cells were treated with $AS_f$ in the presence of D9 (FIG. 5*c*) no increase in ROS production was observed, indicating that the compound of the invention was able to protect SH-SY5Y cells from oxidative stress induced specifically by $AS_f$. Similarly, the positive control doxycycline was also able to protect the cells from oxidative stress (FIG. 5*e*). In addition, neither the presence of D9 nor doxycycline induced intracellular ROS (FIG. 5*d,f*). Quantifications of the results obtained by microscopy are displayed in FIG. 5*g*.

Example 7—Effect of the Compound of the Invention on the Release of the Proinflammatory Cytokine IL-1β

Interleukin-1β (IL-1β) is a potent pro-inflammatory cytokine that is crucial for host-defense responses to infection and injury, and the best characterized and most studied of the 11 IL-1 family members.

To evaluate the effect of Pegasus on LPS-activated microglia, Bv2 cells were pretreated with Pegasus (D9) (200 µM).

After 4 h of treatment, cells were stimulated with LPS (10 μg/mL, final concentration) during 24 h. Doxycycline (Doxy) (200 μM) and Dexamethasone (Dexa) (200 μM) were used as a positive control of anti-inflammatory effects. IL-1β cytokine concentration was measured by ELISA assays (Mouse IL-1 beta ELISA Kit, Cat # BMS6002, Invitrogen), according to instructions provided by the manufacturer.

Figure 6:
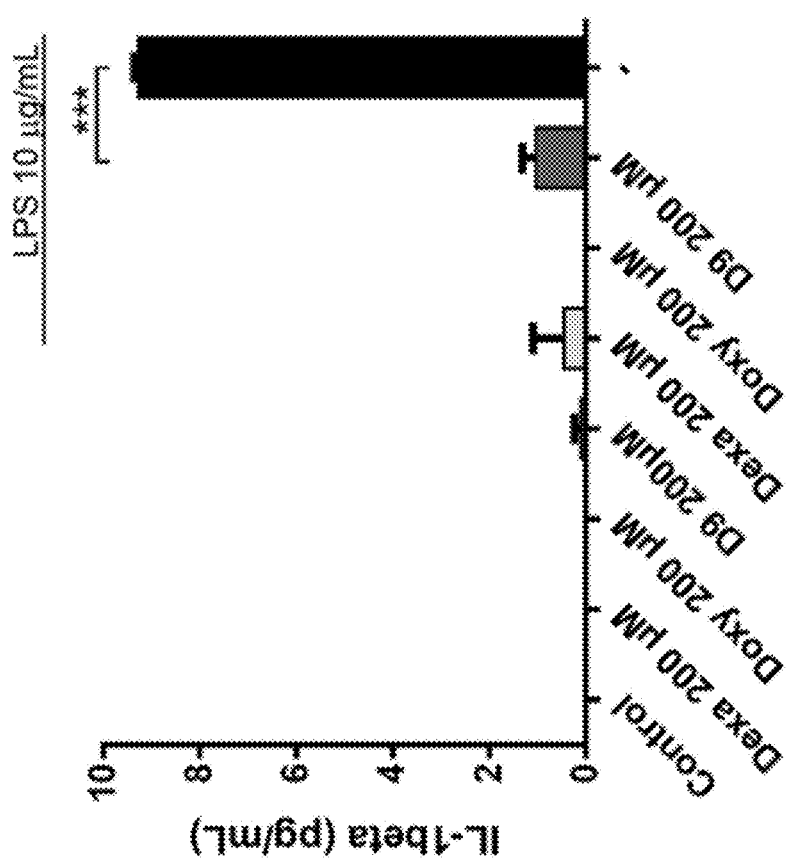
FIG. 6. Proinflammatory cytokine IL-1β assay. The effect of Pegasus (D9) on the release of IL-1β was studied in vitro in LPS-stimulated microglial cells.

Pegasus significantly decreased the inflammatory action of LPS leading to a reduced production of IL-1β. In addition, treatment of Bv2 cells with Pegasus (D9) alone did not lead to a significantly increase of IL-1β release, indicating that this molecule does not exert a pro-inflammatory effect in Bv2 cells (FIG. 6).

Example 8—Effect of Pegasus on Apoptosis in a Transgenic Cytochrome-C-GFP HEK293T Cell Line Model Identification of genes linked to familiar forms of PD have uncovered many molecular pathways involved in neurodegeneration. One of such genes is PTEN-induced kinase 1 (PINK1), a mitochondrial serine/threonine-protein kinase that protects cells from stress-induced mitochondrial dysfunction. PINK1 mutations have been shown to be associated with sporadic PD patients. In fact, PINK1 is the second most frequent causative gene in early-onset PD, where mutations in this gene cause an autosomal recessive form of the disease. Frequent missense or truncating mutations of PINK1 are implicated in the pathogenesis of PARK6 (familial type 6 of PD). Overexpression of wild-type PINK1 has been shown to block mitochondrial release of apoptogenic cytochrome c, caspase-3 activation and apoptotic cell death induced by proteasome inhibitor MG132. N-terminal truncated PINK1 (NΔ35), which lacks a mitochondrial localization sequence, does not block MG132-induced Cytochrome C release and cytotoxicity. Therefore, the release of Cytochrome C from damaged mitochondria is considered a central event in apoptotic signaling. To characterize the ability of Pegasus (D9) to induce mitochondrial damage and apoptosis, as assayed by the release of Cytochrome C from mitochondria, a transgenic Cytochrome C-tGFP HEK293 cell line was used (INNOPROT # P30801) (Goldstein J C, Muñoz-Pinedo C, Ricci J E, et al. Cytochrome C is released in a single step during apoptosis. *Cell Death Differ* 2005; 12(5): 453-62).

The effect of Pegasus on the localization and distribution of mitochondrial Cytochrome C-tGFP was visualized by confocal microscopy after incubation with 200 μM of D9 for 24 hs in the HEK293/Cytochrome C-tGFP cell line (INNOPROT #P30801). Images were acquired in a ZEISS LSM800 Confocal Microscope.

Figure 7:
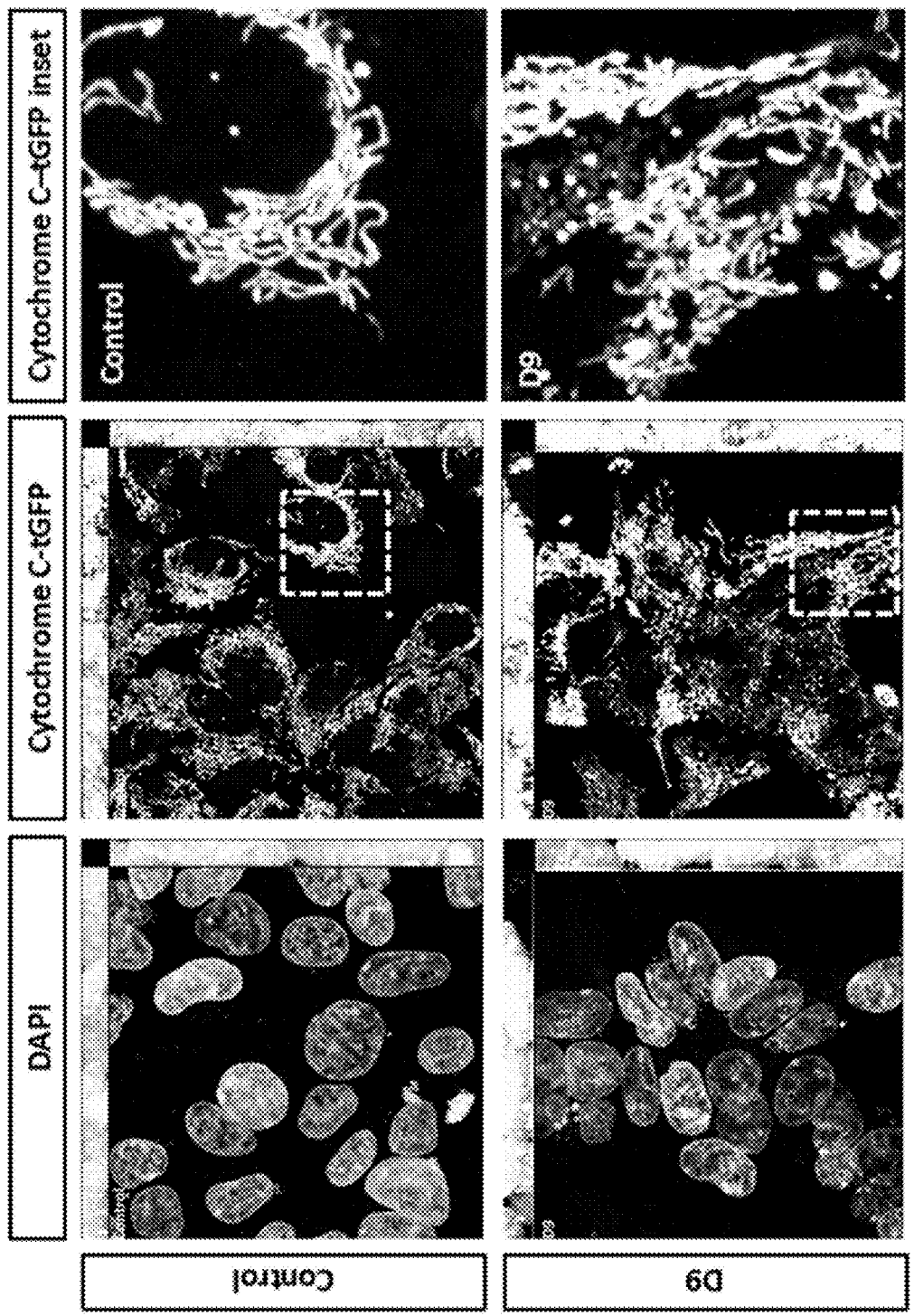
FIG. 7. Apoptosis assay in HEK293T Cytochrome C-tGFP cell line. Confocal microscopy images of Cytochrome C-tGFP after incubation with 200 µM of Pegasus (D9) for 24 hs in the HEK293/Cytochrome C-tGFP cell line.

As shown in FIG. 7, no differences in localization and distribution of Cytochrome C-tGFP, a marker of apoptosis, were observed in the presence or in the absence of 200 μM of Pegasus (D9) after 24 h of incubation between control and Pegasus-treated conditions, as Cytochrome C appeared localized to mitochondrial structures in both cases (FIG. 7, inset).

Example 9—Effect of Pegasus on Lysosomes in the Neuroblastoma Cell Line SH-SY5Y Lysosomes are the final destination of the autophagic pathway. LysoTracker™ fluorescent probes, dyes that preferentially accumulate in vesicles with acidic pH, are widely used for tracing lysosomes in living and fixed cells in order to study organelle localization, their resident proteins, assess organelle functionality, quantify lysosome numbers and abnormalities in vesicular pH (Eskelinen E L, Schmidt C K, Neu S, et al. Disturbed cholesterol traffic but normal proteolytic function in LAMP-1/LAMP-2 double-deficient fibroblasts. *Mol Biol Cell* 2004; 15(7): 3132-45), and to examine the efficiency of autophagosome/lysosome fusion in live cells (González-Polo R A, Boya P, Pauleau A L, et al. The apoptosis/autophagy paradox: autophagic vacuolization before apoptotic death. *J Cell Sci* 2005; 118 (Pt 14): 3091-102.).

The effect of Pegasus on lysosomal activity in SH-SY5Y cells was estimated by visualizing the localization and number of lysosomes, marked by LysoTracker™ Deep Red (ThermoFisher #L12492), after treatment with 200 μM of Pegasus for 24 hs. After incubation, cells were fixed in PFA 4% prepared for confocal microscopy. Images were acquired in a ZEISS LSM800 confocal microscope.

Figure 8:
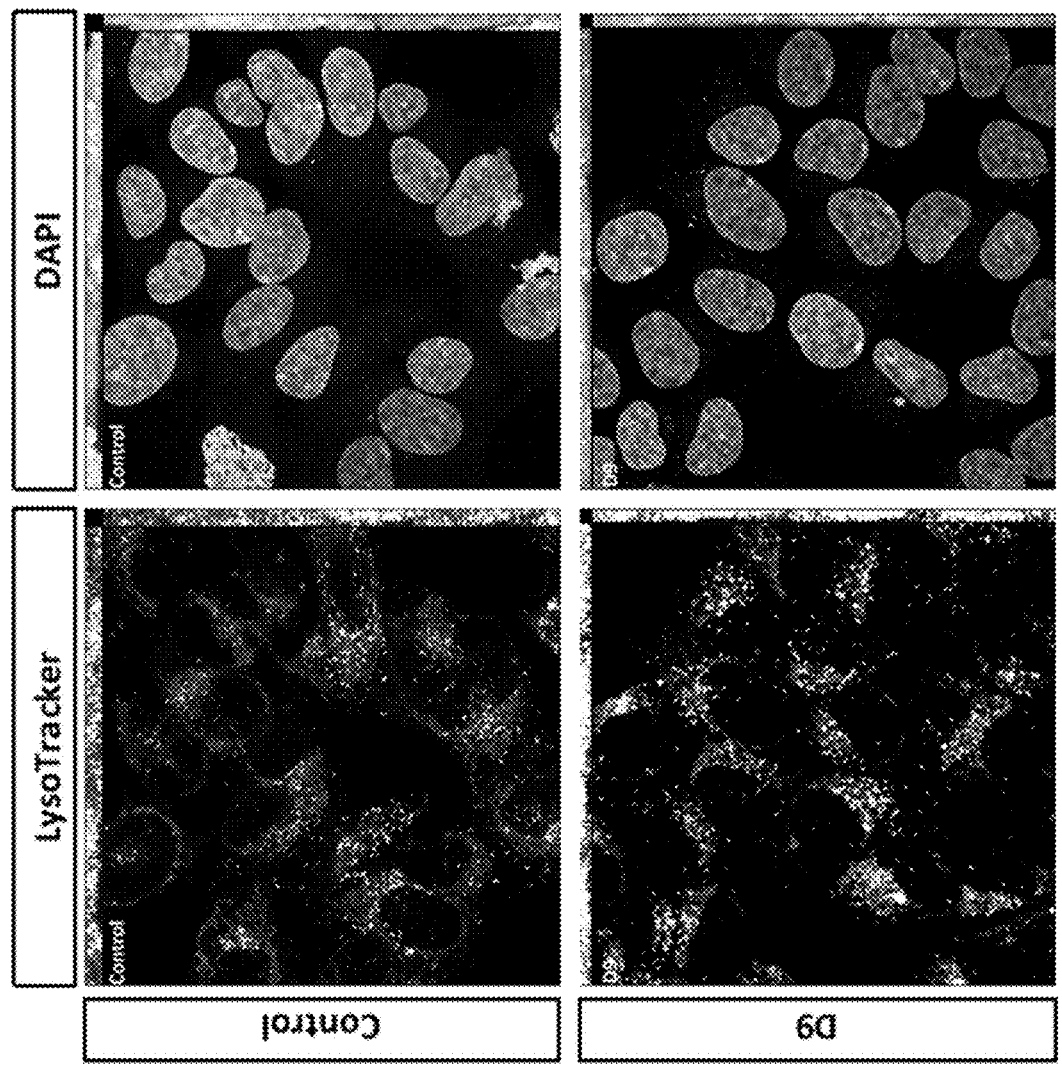
FIG. 8. Effect of Pegasus (D9) on lysosomal activity in SH-SY5Y cells. Confocal microscopy images showing the localization and number of lysosomes after treatment with 200 µM of Pegasus (D9) for 24 hs.

Results suggest that the compound does not interfere with the biogenesis of lysosomes in SH-SY5Y cells, as no apparent differences were observed in SH-SY5Y cells incubated with or without 200 μM of Pegasus (FIG. 8).

Example 10—D1- and D2-Type Receptor Binding Efficiency of the Compound of the Invention Dopamine receptors belong to the superfamily of G protein-coupled seven transmembrane proteins. G-protein-coupled receptors constitute one of the major signal transduction systems in eukaryotic cells. Coding sequences for these receptors, in those regions believed to contribute to the agonist-antagonist binding site, are strongly conserved across mammalian species. Various members of the dopamine receptor family are generally classified as either 'D1-like' or 'D2-like'. D1-like receptors comprise the D1 and D5 receptors, which activate adenylate cyclases via coupling to GS proteins.

The assay was performed by Innoprot S.L. in Spain, evaluating the D1- and D2-type receptor activation efficiency of Pegasus, the intermediate compound DOXI-5, and dopamine as the reference compound, both freshly obtained by the provider and sent along the test compounds to account for any effect possibly caused by the travel conditions of the samples.

Test Compounds
  Pegasus (D9)
  DOXI-5 (D5)
  Test Dopamine (Sigma-Aldrich, reference compound sent along with Pegasus and DOXI-5)
  Fresh Dopamine (Sigma-Aldrich, reference compound obtained at the site of the assay)
Reagents and Equipment
  DMEM (Dulbecco's Modified Eagle's Medium, Sigma-Aldrich, D6429)
  DMEM-F12 (Sigma-Aldrich, D9785)
  Opti-MEM (Opti-Minimal Essential Medium, Thermo-Fisher scientific 31985070, batch 1932076)
  FBS (Fetal Bovine Serum, Sigma-Aldrich F7524, batch BCBW329)
  Flat bottom black 96-well plates (Becton Dickinson 353219, batchE1804340)
Methods
  HEK$_{cAMP}$Nmd_FP650 D1 and U2OS$_{cAMP}$Nmd_FP650_D2 cells were seeded at a density of 30.000 and 20.000 cells/well, respectively, in 96-well plates. Cells were maintained in DMEM or DMEM-F12 medium supplemented with 10% FBS during 24 h at 37° C. in a humidified 5% $CO_2$ atmosphere.

On day 2, cells were treated with 10 serial 1:3 dilutions of Fresh Dopamine, Test Dopamine, Pegasus (D9) or DOXI-5 (D5) compounds diluted in Opti-MEM, starting from 30 µM. Cells were then incubated for 24 h. All the experiments were carried out in triplicate.

To detect Nomad biosensor activation, the assay medium was removed and replaced by 100 ml of DPBS with calcium and magnesium. In the $HEK\_{cAMP}Nmd\_FP650\_D1$ cell line, the agonist effect of the compounds was measured by quantifying the changes in the fluorescence emission of $_{cAMP}$Nomad biosensor using the appropriate filter for the FP650 protein fluorescent signal (excitation/emission max=590/665 nm) in a Sinergy II Biotek microplate reader. In $U2OS\_{cAMP}Nmd\_FP650\_D2$ cells, images were acquired using the CellInsight CX7 HCS Platform, and the number of fluorescent vesicles per cell was quantified with the HCS Studio Cell Analysis Software.

Results

The effect of the compounds in the regulation of D1 or D2 receptors' activation was analyzed measuring the cAMP signaling using the Nomad biosensor-based assay. For the agonist assay, cells were incubated with 10 different concentrations (1:3 serial dilutions starting from 30 µM) of Fresh Dopamine, Test Dopamine, Pegasus (D9) or DOXI-5 (D5) dissolved in Opti-MEM for 24 hours.

Figure 9:
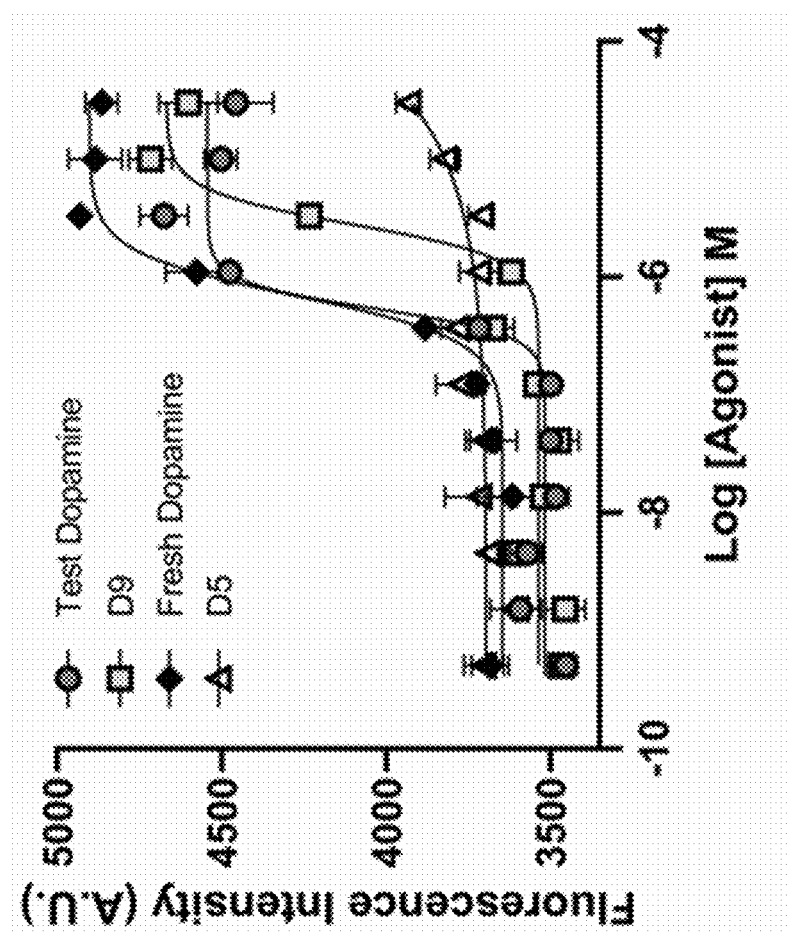
FIG. 9. Activation of D1 dopamine receptors by Pegasus (D9). Dose-response curves in the $HEK_{cAMP}Nmd\_DRD1$ cell line. Cells were treated with Fresh Dopamine (diamonds), Test Dopamine (circles), Pegasus (D9) (squares) or D5 (triangles) for 24 hours. Data points represent the mean±SD for each condition for a single experiment performed in triplicate.

In the HEK_cAMPNmd_FP650_D1, the effect of the compounds was analyzed measuring the changes in fluorescence intensity using the Synergy II Biotek microplate reader (FIG. 9).

The results showed that Fresh Dopamine exhibited an EC50 of $5.48\times10^{-7}$ M. Similarly, Test Dopamine showed an EC50 of $6.92\times10^{-7}$ M. In the case of Pegasus, the efficacy of the compound to activate the D1 receptor decreased one order of magnitude, with an EC50 of $2.8\times10^{-6}$ M. Finally, DOXI-5 (D5) did not act as an agonist of the D1 receptor, as it caused no activation of the Nomad biosensor.

Figure 10:
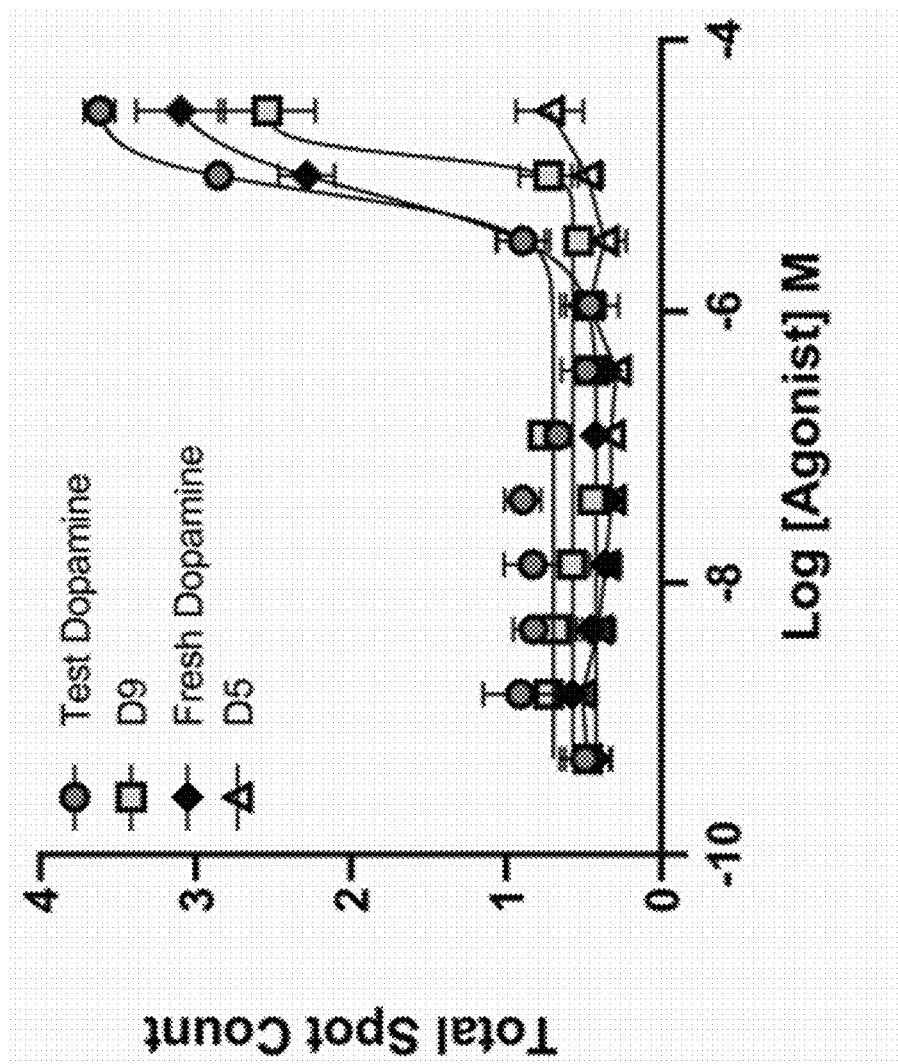
FIG. 10. Activation of D2 dopamine receptors by Pegasus (D9). Dose-response curves in the $U2OS_{cAMP}Nmd\_DRD2$ cell line. Cells were treated with Fresh Dopamine (diamonds), Test Dopamine (circles), Pegasus (D9) (squares) or D5 (triangles) for 24 hours. Data points represent the mean±SD for each condition for a single experiment performed in triplicate.

This same experiment was carried out in the U2OS_cAMPNmd_FP650_D2 cell line (FIG. 10). The effect of the compounds was analyzed quantifying the number of fluorescent vesicles in the cytoplasm of the cells using the HCS Studio Cell Analysis Software.

In this case Fresh Dopamine showed an EC50 of $7.44\times10^{-6}$ M, similar to the EC50 of Test Dopamine ($7.2\times10^{-6}$ M). Pegasus showed an EC50 of $1.13\times10^{-5}$ M, while DOXI-5 (D5) did not act as an agonist of the D2 receptor, as it caused no activation of the Nomad biosensor.

CONCLUSIONS

The compounds Pegasus (D9) and DOXI-5 (D5) have very similar effects in both D1 and D2 functional assays.

The travel conditions did not significantly affect the capability of dopamine to act as an agonist to D1 and D2.

Pegasus (D9) exhibits agonistic capabilities of both D1 and D2 receptors, although to a somewhat lesser degree than dopamine.

DOXI-5 (D5) is not an agonist of D1 or D2 receptors as it does not induce the activation of the Nomad biosensors.

What is claimed is:

1. A compound comprising a modified tetracycline derivative, covalently coupled through a linker to dopamine, wherein the compound is defined by the following formula:

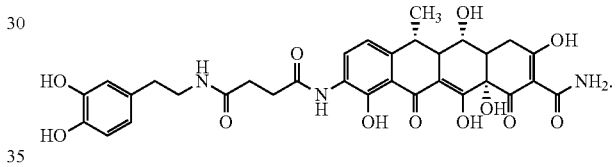

2. A pharmaceutical composition comprising the compound of claim 1, and one or more pharmaceutically acceptable excipients.

* * * * *